United States Patent [19]

Stambler

[11] Patent Number: 5,646,998
[45] Date of Patent: Jul. 8, 1997

[54] SECURE TRANSACTION SYSTEM AND METHOD UTILIZED THEREIN

[76] Inventor: Leon Stambler, 7803 Boulder La., Parkland, Fla. 33067

[21] Appl. No.: 445,477

[22] Filed: May 22, 1995

Related U.S. Application Data

[62] Division of Ser. No. 122,071, Sep. 14, 1993, Pat. No. 5,524,073, which is a division of Ser. No. 977,385, Nov. 17, 1992, Pat. No. 5,267,314.

[51] Int. Cl.$^6$ ............................................. H04L 9/00
[52] U.S. Cl. .................................... 380/25; 380/24
[58] Field of Search .................. 380/23–25; 340/825.34

[56] References Cited

U.S. PATENT DOCUMENTS

| | | | |
|---|---|---|---|
| 3,609,690 | 9/1971 | Nissman | 340/149 R |
| 3,611,293 | 10/1971 | Constable | 340/149 A |
| 3,657,521 | 4/1972 | Constable | 235/61.7 B |
| 3,892,948 | 7/1975 | Constable | 340/149 A |
| 3,938,091 | 2/1976 | Atalla et al. | 340/149 A |
| 4,004,089 | 1/1977 | Richard et al. | 178/22 |
| 4,016,405 | 4/1977 | McCune et al. | 235/380 |
| 4,186,871 | 2/1980 | Anderson et al. | 235/380 |
| 4,198,619 | 4/1980 | Atalla | 340/149 A |
| 4,200,770 | 4/1980 | Hellman et al. | 380/30 |
| 4,208,575 | 6/1980 | Haltof | 235/380 |
| 4,223,403 | 9/1980 | Konheim et al. | 375/2 |
| 4,234,932 | 11/1980 | Gorgens | 364/900 |
| 4,264,782 | 4/1981 | Konheim | 178/22 |
| 4,268,715 | 5/1981 | Atalla | 178/22 |
| 4,281,215 | 7/1981 | Atalla | 178/22.08 |
| 4,283,599 | 8/1981 | Atalla | 178/22.1 |
| 4,302,810 | 11/1981 | Bouricius et al. | 380/24 |
| 4,304,990 | 12/1981 | Atalla | 235/380 |
| 4,317,957 | 3/1982 | Sendrow | 178/22.08 |
| 4,328,414 | 5/1982 | Atalla | 235/380 |
| 4,386,266 | 5/1983 | Chesarek | 235/380 |
| 4,405,829 | 9/1983 | Rivest et al. | 380/30 |
| 4,498,000 | 2/1985 | Decavale et al. | 235/380 |
| 4,590,470 | 5/1986 | Koening | 340/825.31 |
| 4,605,820 | 8/1986 | Campbell, Jr. | 380/24 |
| 4,665,396 | 5/1987 | Dieleman | 380/23 |
| 4,686,357 | 8/1987 | Douno et al. | 235/379 |
| 4,720,859 | 1/1988 | Aaro et al. | 380/23 |
| 4,734,858 | 3/1988 | Schlafly | 364/408 |
| 4,747,050 | 5/1988 | Brachtl et al. | 380/24 |
| 4,755,940 | 7/1988 | Brachtl et al. | 364/408 |
| 4,797,920 | 1/1989 | Stein | 380/24 |
| 4,799,061 | 1/1989 | Abraham et al. | 340/825.34 |
| 4,908,861 | 3/1990 | Brachtl et al. | 380/25 |
| 4,928,098 | 5/1990 | Dannhaeuser | 340/825.56 |
| 4,933,969 | 6/1990 | Marshall et al. | 380/125 |
| 4,935,962 | 6/1990 | Austin | 380/25 |
| 4,947,028 | 8/1990 | Gorog | 235/381 |
| 4,965,568 | 10/1990 | Atalla et al. | 380/24 |
| 4,977,595 | 12/1990 | Ohta et al. | 380/24 |
| 4,992,783 | 2/1991 | Zdunek et al. | 340/825.34 |
| 5,016,274 | 5/1991 | Micali et al. | 380/23 |
| 5,023,908 | 6/1991 | Weiss | 380/21 |
| 5,163,098 | 11/1992 | Dahbura | 380/24 |
| 5,168,520 | 12/1992 | Weiss | 380/23 |
| 5,196,840 | 3/1993 | Leith et al. | 340/825.34 |
| 5,199,066 | 3/1993 | Logan | 380/4 |
| 5,267,314 | 11/1993 | Stambler | 380/25 |
| 5,341,428 | 8/1994 | Schatz | 380/23 |
| 5,367,572 | 11/1994 | Weiss | 380/23 |

*Primary Examiner*—Salvatore Cangialosi
*Attorney, Agent, or Firm*—Panitch Schwarze Jacobs & Nadel, P.C.

[57] ABSTRACT

A transaction system is disclosed wherein, when a transaction, document or thing needs to be authenticated, information associated with one or more of the parties involved is coded together to produce a joint code. This joint code is then utilized to code information relevant to the transaction, document or record, in order to produce a variable authentication number (VAN) at the initiation of the transaction. This VAN is thereafter associated with the transaction and is recorded on the document or thing, along with the original information that was coded. During subsequent stages of the transaction, only parties capable of reconstructing the joint code will be able to uncode the VAN properly in order to re-derive the information. The joint code serves to authenticate the parties, and the comparison of the re-derived information against the information recorded on the document serves to authenticate the accuracy of that information.

23 Claims, 15 Drawing Sheets

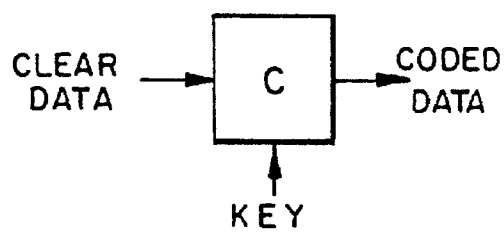
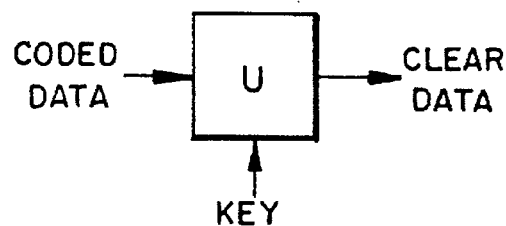
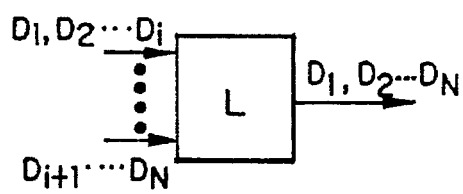
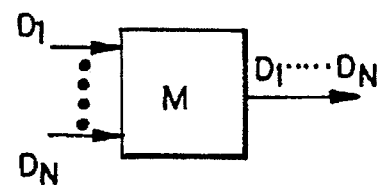
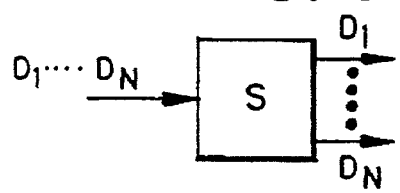
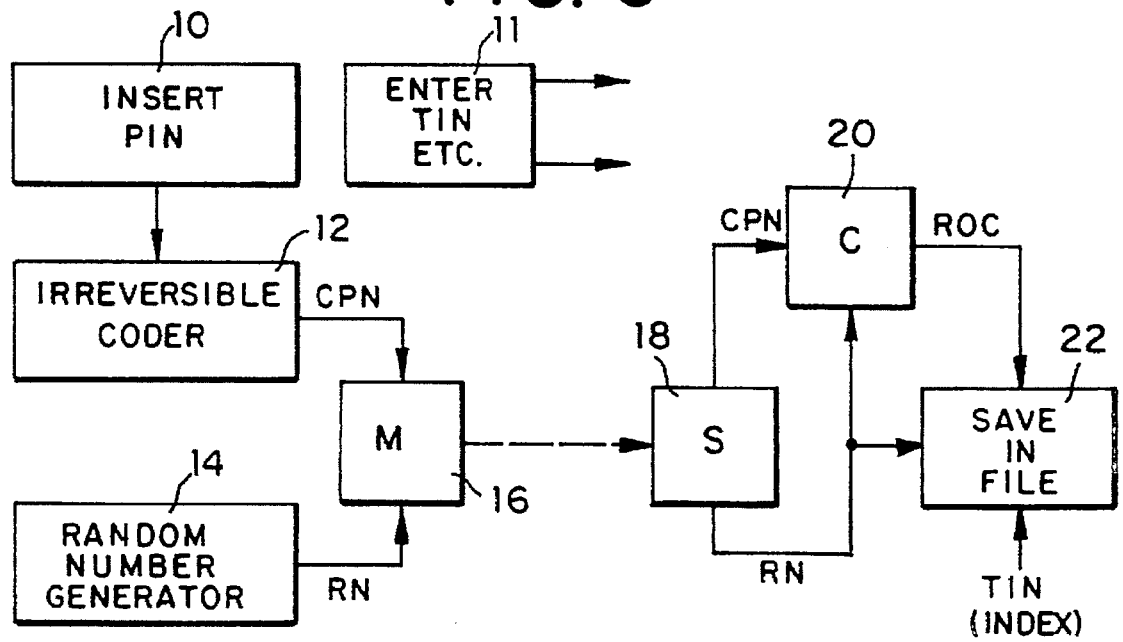

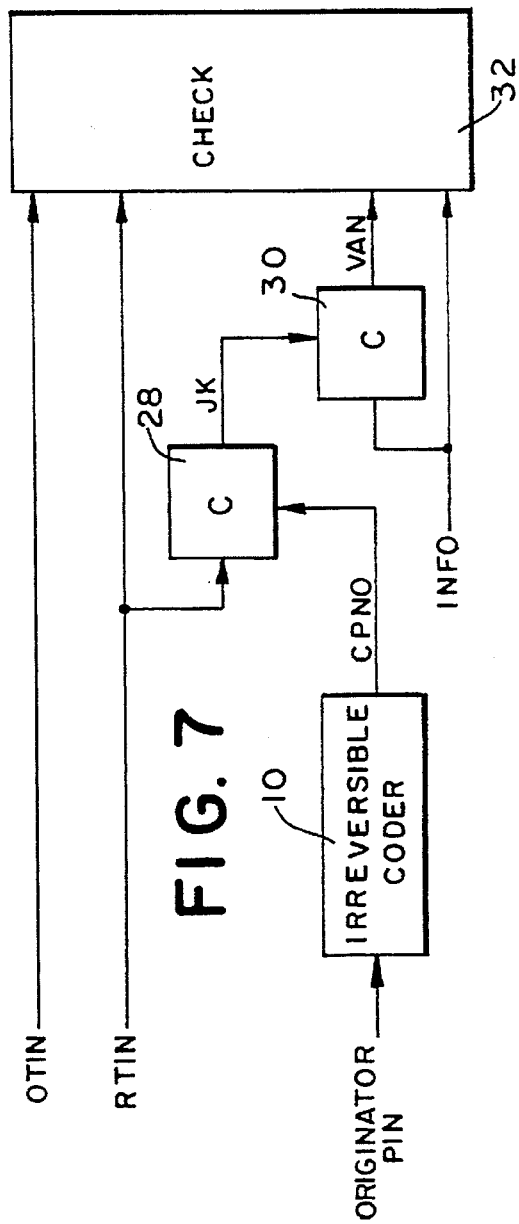
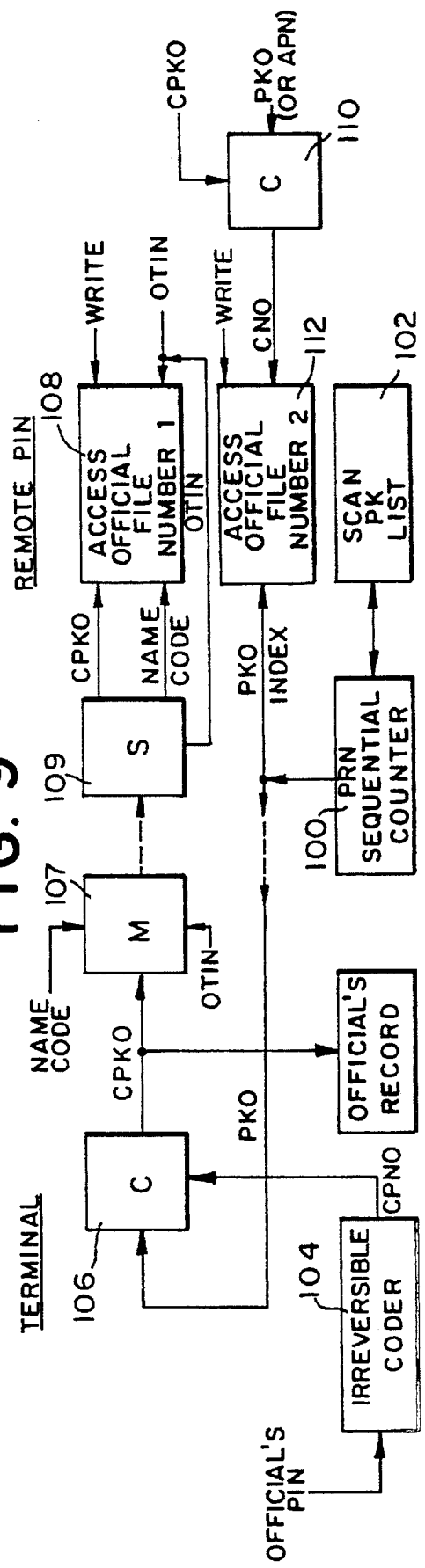

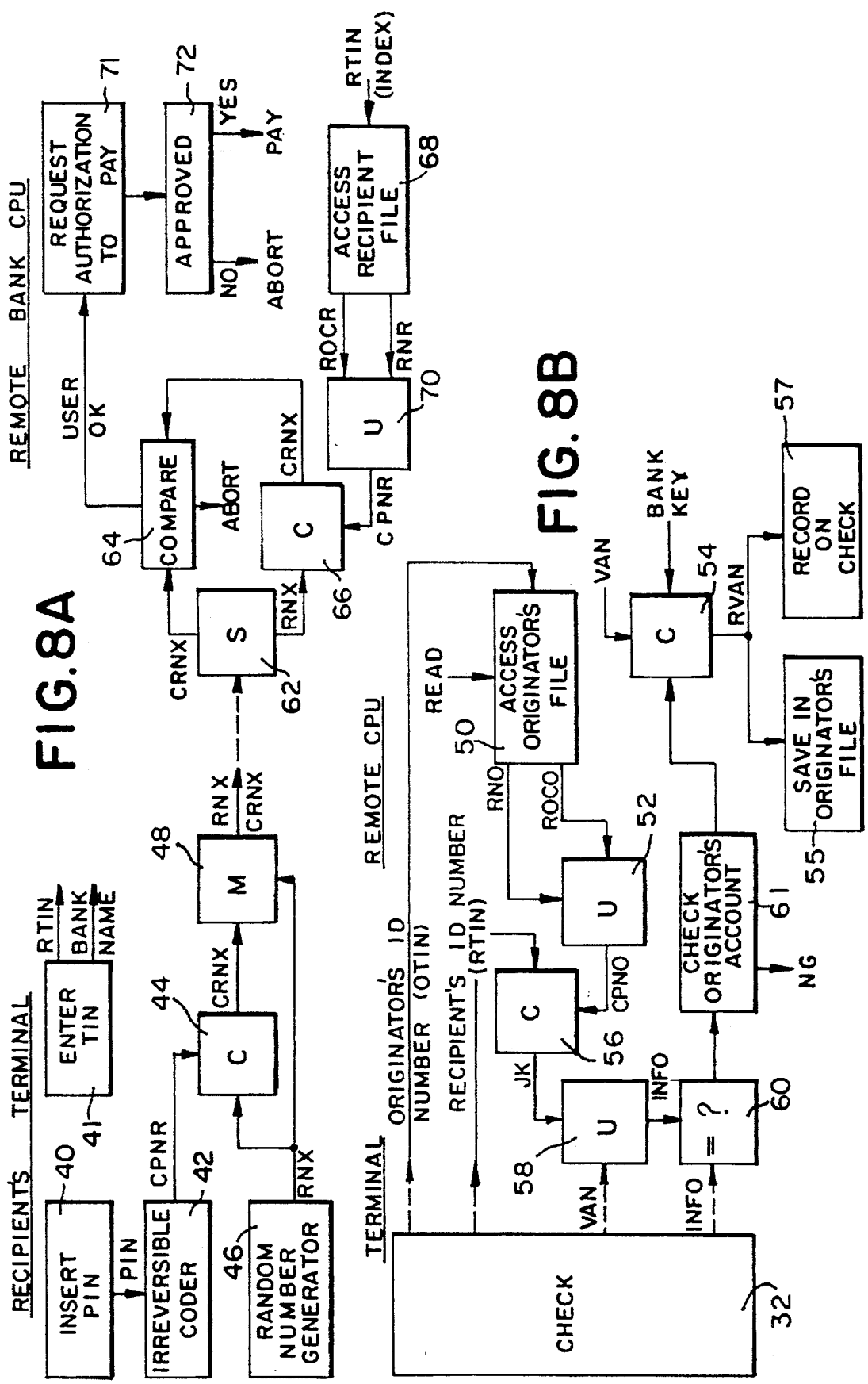

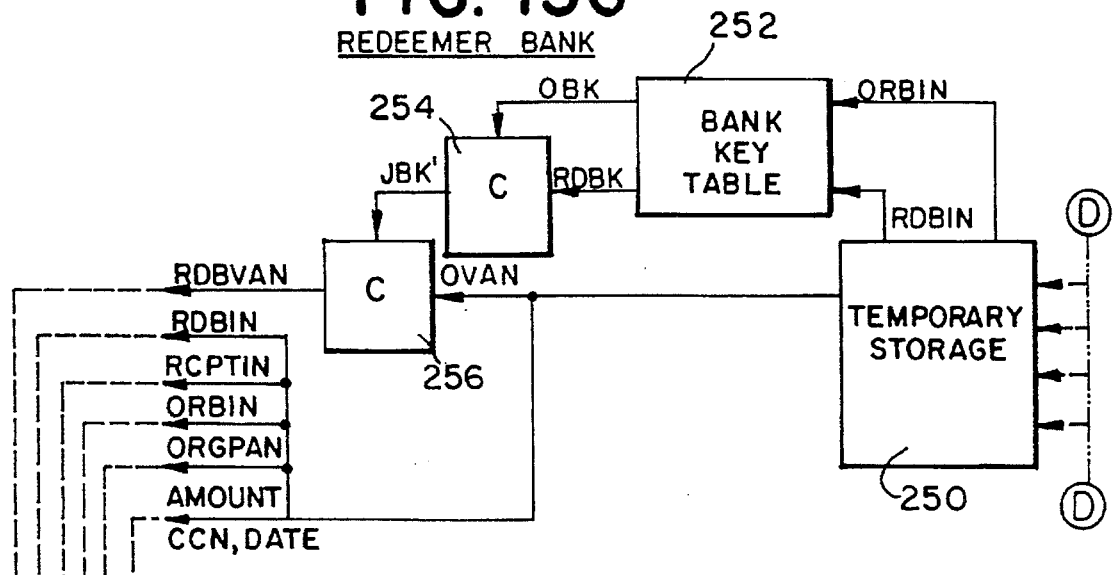
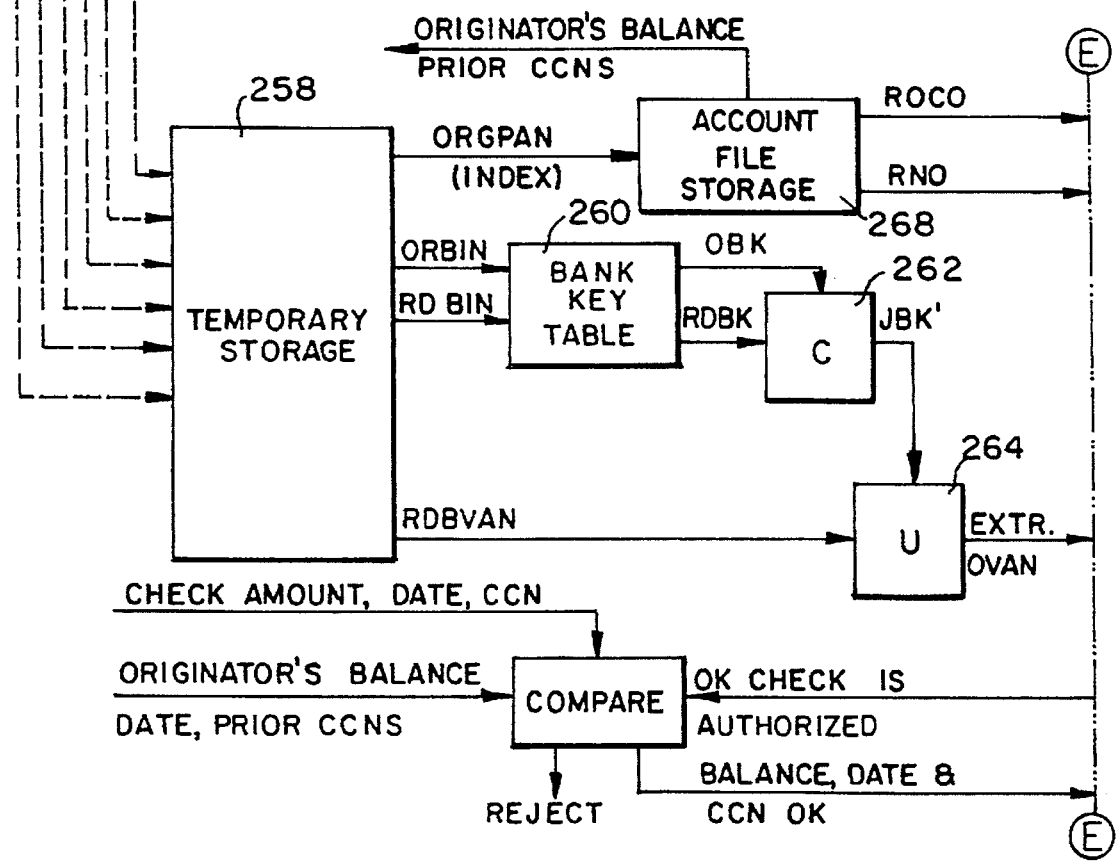
FIG. 13C

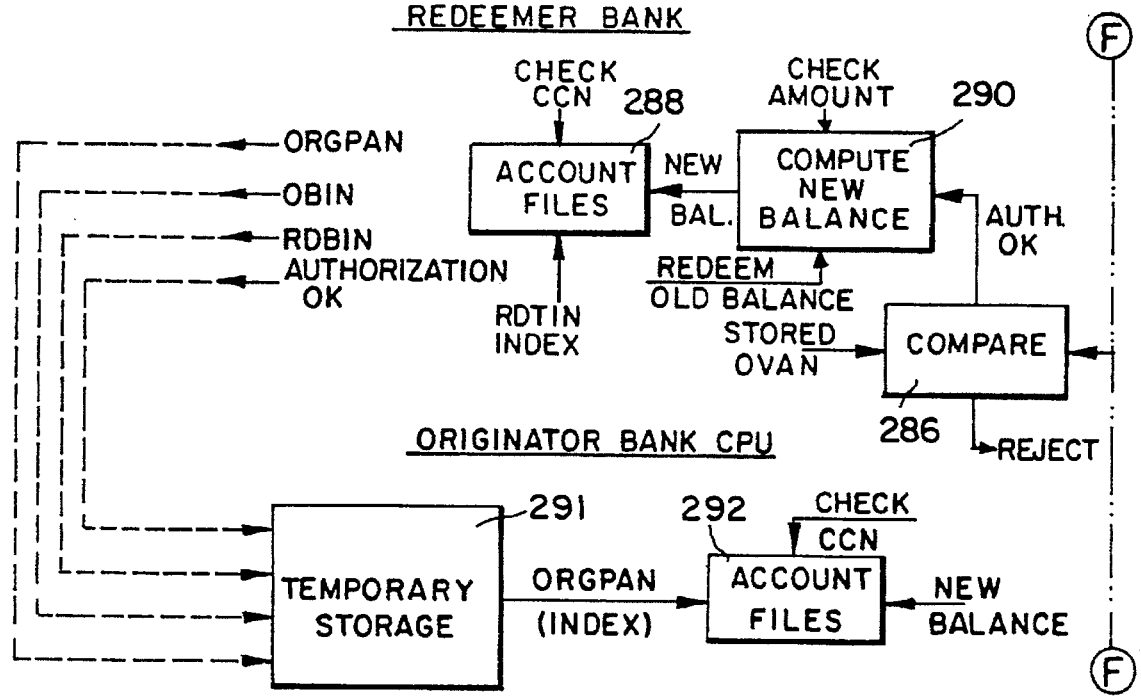
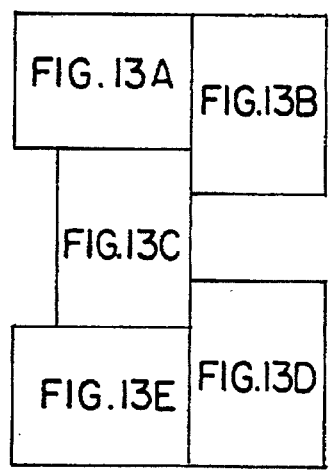

5,646,998

SECURE TRANSACTION SYSTEM AND METHOD UTILIZED THEREIN

This is a division of U.S. patent application Ser. No. 08/122,071, filed Sep. 14, 1993, now U.S. Pat. No. 5,524,073 which is a division of U.S. patent application Ser. No. 07/977,385, filed Nov. 17, 1992, which has now issued as U.S. Pat. No. 5,267,314.

FIELD OF THE INVENTION

The present invention relates generally to secure transaction systems and, more particularly, concerns a method and apparatus for authenticating documents, records and objects as well as the individuals who are involved with them or responsible for them.

BACKGROUND OF THE INVENTION

There are many times in our daily lives when the need arises for highly secure transactions. For example, instruments of commerce, such as checks, stock certificates, and bonds are subject to theft and forgery. From the time a document is issued, the information contained on it, or the name of the recipient could be changed. Similarly, passports, pay checks, motor vehicle registrations, diplomas, food stamps, wager receipts, medical prescriptions, or birth certificates and other official documents are subject to forgery, fraudulent modification or use by an unintended recipient. As a result, special forms, official stamps and seals, and special authentication procedures have been utilized to assure the authenticity of such documents. Medical, legal and personnel records, and all types of information in storage media are also subject to unauthorized access. Passwords and coding of such records have been used to thwart unauthorized access. However, there have always been ingenious individuals who have somehow managed to circumvent or evade all such systems of security.

With the introduction of computers and computer communications into business transactions and document processing, a certain degree of security was gained, in that it is now possible to verify documents and transactions much more quickly, thereby avoiding many frauds which previously went unnoticed until it was too late. However, with the elimination of the human factor, verification of the identify of parties also became more difficult. A pressing need still exists for business transaction, document processing and record access systems which can assure the identity of the parties and the accuracy of the information involved in the transaction. As used herein, the term "record access systems" includes systems which access media which contains data, messages, text, FAX, audio, video, drawings, images, photo, electronic and physical mail, safe boxes, and the like. As used herein the term "business transaction system" will be intended as a generic term to describe all such transaction, document processing and record access systems, including ones not related to business use, such as passport authentication systems.

The security problems described above have been handled with some degree of success in systems involving a single party transaction where the party is present. For example, during the use of an automatic teller machine, the customer is the sole party involved and is present in person. However, until the present invention, it has not been possible to verify the identity and to secure the interests of all parties to multi-party transactions and, in particular, absent parties to a transaction.

SUMMARY OF THE INVENTION

Briefly, the present invention is directed to a transaction, document processing, or record access system which avoids the shortcomings of known systems of this type. In accordance with an embodiment of the present invention, when a transaction, document or thing needs to be authenticated, information associated with at least one of the parties involved (e.g., an originator and/or a recipient) is coded to produce a joint code. This joint code is then utilized to code information relevant to the transaction, document or record, in order to produce a variable authentication number (VAN) or code at the initiation of the transaction. This VAN is thereafter associated with the transaction and is recorded on the document or thing, along with the original information that was coded. During subsequent stages of the transaction, only parties capable of reconstructing the joint code will be able to uncode the VAN properly in order to re-derive the information. Thus, the joint code serves to authenticate the parties, and the comparison of the re-derived information against the information recorded on the document serves to authenticate the accuracy of that information. Alternatively, the information could be authenticated by regenerating a VAN from the recorded information and comparing the regenerated VAN with the recorded VAN.

In accordance with an embodiment of the present invention, at the time of enrolling as a user of the system, each user selects a personal identification number (PIN), which is secret, does not exist in an uncoded form, and cannot be recovered from other information anywhere in the system. During or after enrollment, a non-secret identification code and a secret code are also stored in a user's file at the user associated computer facility. When a user participates in a transaction, the user is required to utilize his or her PIN, which after being coded is used to derive a coded arbitrary number. Subsequently, this arbitrary code is compared to another such code which is generated from a reconstituted version of the coded PIN, in order to authenticate the user's identity. One of the embodiments creates a computer file with a secret address to authenticate a user's identity, and to secure sensitive records. The address is preferably not stored anywhere in the system, but is generated when needed from information supplied by the user. In some embodiments of the present invention, when a joint code is created as described above, one participating user (e.g., the originator) must provide his or her PIN. The other party's non-secret identification code and the PIN are utilized in creating the joint code. In other embodiments, the joint code is created from the coded PIN's of the participants.

BRIEF DESCRIPTION OF THE DRAWINGS

The foregoing brief description as well as further objects, features, and advantages of the present invention will be understood more completely from the following detailed description of the presently preferred, but nonetheless illustrative, embodiments of the invention, with reference being had to the accompanying drawings, in which:

FIGS. 1–5 illustrate the symbols utilized in the present application to represent conventional building blocks used to form the invention, these building blocks being respectively, a coder, an uncoder, a linker, a mixer, and a sorter;

FIGS. 6–8 are functional block diagrams illustrating a check transaction system in accordance with a first embodiment of the present invention, with FIG. 6 illustrating user enrollment, FIG. 7 illustrating how an originator generates a check, and FIGS. 8A and 8B illustrating the authentication process when the check is presented to be cashed;

FIGS. 9–12 are functional block diagrams illustrating a credential issuing and authentication system in accordance with a second embodiment of the present invention, with FIG. 9 illustrating the enrollment of an official, FIG. 10 illustrating the enrollment of a user, FIG. 11 illustrating the issuance of the credential, and FIG. 12 illustrating the authentication of an issued credential;

FIGS. 13A–13E, when arranged as illustrated in FIG. 14, collectively represent a functional block diagram of a check transaction system similar to that of FIGS. 6–8, but including the basic processing necessary to clear and pay a check electronically;

DETAILED DESCRIPTION OF THE PREFERRED EMBODIMENTS

Figure 10A:
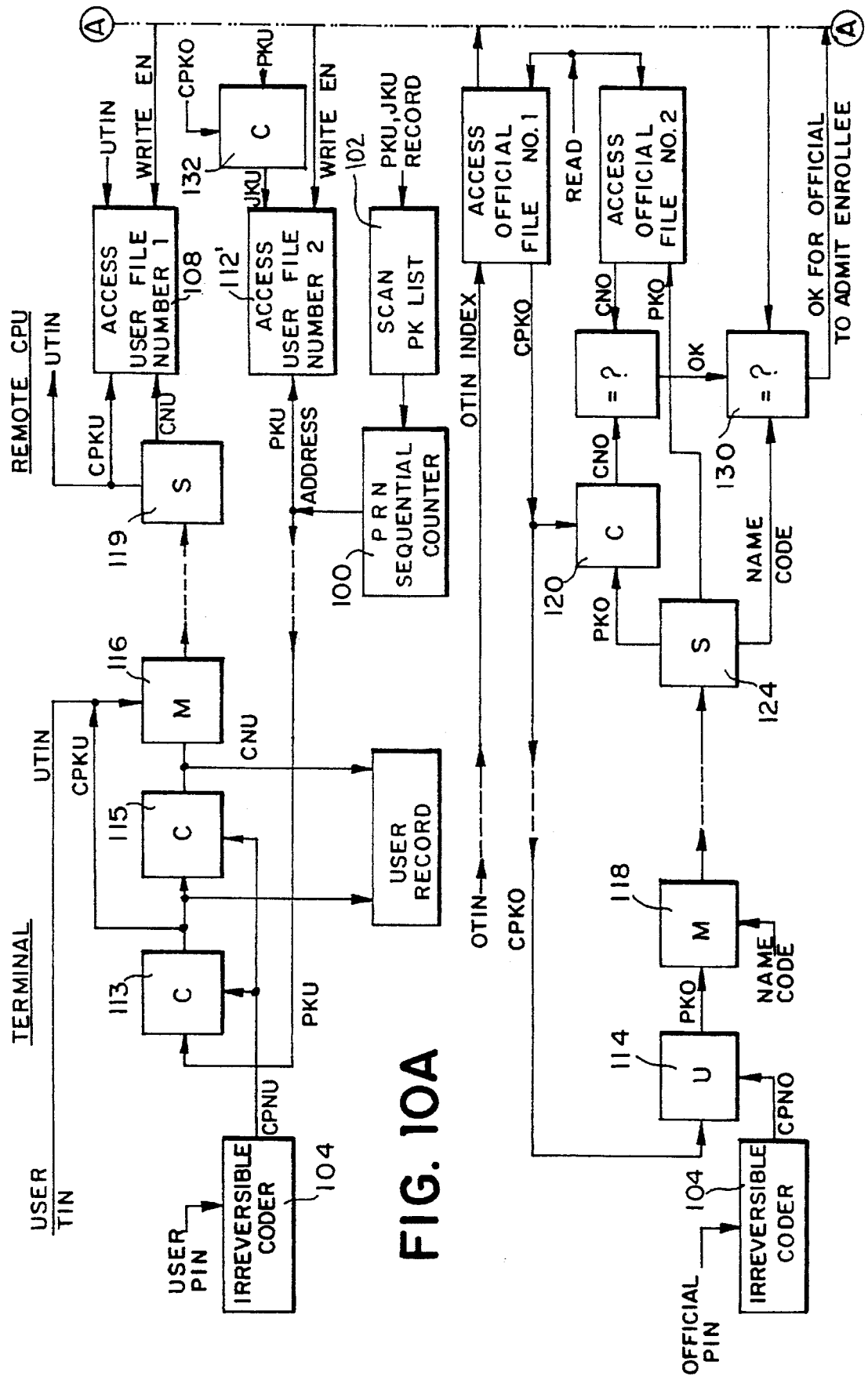

FIGS. 1–5 illustrate the functional building blocks utilized in the preferred embodiments. All of these components are conventional building blocks for computer or communication systems. Moreover, those skilled in the art will appreciate that the blocks can be realized as hardware components, or they can be realized as functional blocks in an overall computer program.

The coder illustrated in FIG. 1 and the uncoder illustrated in FIG. 2 may be any form of such device utilizing a known algorithm, such as the Data Encryption Standard (DES). A coder, as illustrated in FIG. 1, has at least one data input, at which it receives clear data. It also has one or more additional inputs for receiving keys $K_1$, $K_2$, which are utilized to code the clear data into a form in which it could not be easily recognized or uncoded without the use of the keys. A variable which is used as a key may be padded to obtain the desired security. An uncoder (FIG. 2) reverses the process of the coder. Basically, it receives the coded data and utilizes the same keys to reconstruct the clear data.

A linker (FIG. 3) receives a plurality of data inputs and concatenates them into a longer code word ($D_1, D_2 \ldots D_N$). Similarly, a mixer (FIG. 4) receives a plurality of data inputs ($D_1$, and $D_2$ through $D_N$) and mixes their digits or binary bits. A simple example of a mixer would be a conventional time division multiplexer which is used to interleave plural data inputs. However, in many applications, it will be preferable to utilize a more sophisticated mixer, such as one that utilizes arithmetic and logical combinations of digits or bits. A sorter (FIG. 5) reverses the process of a linker or a mixer, that is, it receives a concatenated or mixed code word and reproduces the original component words. A time division de-multiplexer could serve as a sorter for a mixed signal originally generated by a multiplexer.

FIGS. 6, 7, 8A and 8B constitute a functional block diagram illustrating the present invention in a check transaction system. The system illustrated in FIGS. 6, 7, 8A and 8B are well suited for use in generating and processing employee paychecks, for example. The system involves three phases of operation. In the first phase, illustrated in FIG. 6, a user of the system must enroll in order to be recognized by the system. Each user enrolls at his or her bank, or at another convenient location, such as a place of employment, in the presence of an officer, who appropriately verifies the user's identity and obtains the typical information from him, including his taxpayer identification number (TIN) and telephone number. An account is then opened for the user and a file is created for him or her in the bank's computer, and the bank assigns a person account number (PAN) to the user's account. If a bank card is issued to the user, it usually contains the PAN and a bank identification number (BIN).

While operating a terminal, the user is requested to select a personal identification number (PIN) and to enter that PIN into the terminal. The user complies and such entry occurs at block 10 of FIG. 6 with the typical transaction information, including the user's TIN or PAN, being entered at block 11. The PIN is applied directly to an irreversible coder 12, where it is processed to produce a coded PIN (CPN). Coder 12 may be any type of conventional coding device which can process the PIN so that the coding is irreversible (i.e., the PIN cannot be recovered from the CPN). At the same time, a random number generator 14 produces a random number (RN), which is applied to a mixer 16 along with the CPN. Alternately, the user may be permitted to select an arbitrary number for RN.

The signal produced by mixer 16 is then transmitted to the bank's computer, where it is applied to a sorter 18. It is assumed that this transmission preferably occurs over a secure line, such as one protected by a tandem coder and uncoder which can utilize a joint terminal-bank key. The sorter recovers the original CPN and RN, saving RN in the user's file at block 22. It should be noted that in saving RN, the user's file is accessed by using his TIN as an index. The received CPN is applied as the data input to a coder 20, which receives RN as its key input, producing a revisable owner code (ROC) which is saved in the user's file in the same manner as RN. Various additional information is saved in the user's file, such as his personal account number (PAN), name, phone number (PHN), account balance, and other relevant information. The user's TIN, PAN or PHN can be used as an index to access the user's file. CPN represents coded authentication information since it is a coded form of the PIN, and since it is used in other parts of the system to authenticate the user and the transaction. The system preferably maintains RN as a secret number (although in the present embodiment the user file is not secret since it is accessed using a non-secret index) and ROC is maintained as a non-secret number. As explained in detail below, CPN is derivable from ROC and RN.

FIG. 7 illustrates how the originator generates a check in accordance with the present invention. This process preferably takes place at the originator's terminal or computer. It is assumed that the originator would be generating a check in the usual manner and would include on it all of the information usually found on a check, as well as the information normally recorded or imprinted on check forms, such as the recipient's name and TIN (RTIN), and the originator's personal account number and bank identification number. Preferably, the terminal includes a check reader and printer which can read necessary information from the originator's check form and print information on the form, although this could also be done manually by the originator. The originator and the recipient can be the same person, for example, where a person is cashing a personal check originated by the person. In the case of multi-party checks, the check is originated by a present party (i.e., the originator) in favor of an absent party (recipient).

The originator enters his or her PIN at a terminal or computer. Through irreversible coder 10, the originator's PIN is converted to a coded PIN (CPNO), which is applied as the key input to coder 28. The data input to coder 28 is the recipient's TIN (RTIN), which has been read from the check, or accessed from the computer memory, or entered by the originator. The data output of coder 28 is a joint key (JK), which is applied as the key input to a coder 30. Generally, the JK is generated using information associated with at least one of the parties involved in the transaction (in this case, the originator and recipient). As will be shown more fully below, the joint key (or code) is used to protect and authenticate the originator and recipient. The data input to the coder 30 is the information (INFO) to be authenticated (that is, information relevant to the transaction, such as check number, amount, etc.).

The data output of the coder 30 is a variable authentication number (VAN), which codes the information to be authenticated, based upon information related to the recipient and information related to the originator. Note that the VAN is alternatively generated directly from INFO and information associated with at least one of the parties, without the intermediate step of generating the JK. The VAN and at least a portion of the information relevant to the transaction are written or imprinted upon the check 32, thereby becoming a permanent part of it. Alternately, the check may represent an electronic transfer of funds or some other type of electronic transaction. In this case, the VAN and at least a portion of the information relevant to the transaction are included with the electrical signals associated with the electronic transaction.

It is contemplated that in creating the VAN, all information would not necessarily be coded in the same manner. For example, the amount of the check might be considered important enough so as to be recoverable completely, and it would be coded into the VAN in a manner that would permit complete recovery. Other information, such as the date and check control number might be considered less important and would be coded into the VAN in such a manner as to permit detection of changes (e.g., error detection coding), but without complete recovery of the original information.

As noted above, other predetermined information which is known jointly by the originator and recipient, and which does not appear on the check, can also be used to derive the VAN. For example, when a check is drawn to multiple recipients, e.g., husband and wife, each recipient's TIN (which does not appear on the check) may be used to derive the joint code and VAN. This makes it more difficult to fraudulently generate the VAN since the predetermined information not appearing on the check would not be generally known.

FIGS. 8A and 8B illustrate the authentication process at a terminal when the recipient presents the originator's check to be cashed. The terminal communicates via a network of the banks involved in the transaction. Preferably, the terminal includes a device which can read information directly from the check 32. Alternately, the terminal operator can manually key information into the terminal, based upon information appearing on the face of the check 32. At block 40, the recipient inserts his or her PIN, and at block 41, identifies his bank and enters his TIN (RTIN) and all information required by the terminal to initiate the transaction. An irreversible coder 42 processes the PIN to produce the coded PIN, CPNR, which is applied as the key input to a coder 44. A random number generator produces a random number (i.e., an arbitrary number) RNX which is applied as the data input to coder 44. Coder 44 then produces a coded random number (i.e., a coded arbitrary number), CRNX, which is applied to mixer 48 along with RNX. The output of the mixer is, therefore, a signal which contains CRNX and RNX in a converted form, so that neither number nor CPNR may readily be discerned from the signal. CRNX represents coded authentication information because it is a coded representation of CPNR, and because it is used by the system to authenticate the recipient and the transaction.

The mixer signal, along with the information entered in block 41 and the information read from the check are transmitted to the computer at the recipient's bank (i.e., remote bank CPU) over preferably an unsecured line (the use of an unsecured line is possible because CRNX and RNX, not CPNR, are transmitted from the mixer 48 to the sorter 62). The system first authenticates the identify of the check holder at the recipient's bank. Next, the information on the check, as well as the originator and recipient, are authenticated at the originator's bank.

At the recipient's bank, the output of mixer 48 is received in a sorter 62, which separates CRNX and RNX, with CRNX being applied to a comparison block 64 and RNX being applied as the data input to a coder 66. Based upon the recipient's TIN, RTIN, his bank's computer is able to access his file at block 68 and to extract his ROC (a non-secret number) and RN (a secret number), ROCR and RNR therefrom. ROCR and RNR are applied as the data and key inputs, respectively, to an uncoder 70, which generates the recipient's CPN, CPNR, which is applied as the key input to coder 66. Coder 66, therefore, reproduces the recipient's coded random number, CRNX (in the same manner as coder 44), which is applied as the second input to comparison block 64. It should be appreciated that the CPNR output of uncoder 70 is the true CPNR derived from the bank's records. Accordingly, the CRNX produced by coder 66 is the true CRNX. Therefore, should the comparison at block 64 fail, the authentication of the recipient has failed and it is presumed that recipient is not the party presenting the check. The transaction is therefore aborted. On the other hand, if the recipient's identity is authenticated, the transaction can proceed. The recipient's bank then communicates with the originator's bank, conveying all the information about the transaction and requesting authorization to pay (block 71).

As shown in FIG. 8B, at the originator's bank, using OTIN (or the originator's PAN) as an index, the originator's ROCO and random number, RNO, are extracted from the originator's file at block 50. ROCO is applied as the data input to an uncoder 52, and RNO is applied as the key input to uncoder 52. Uncoder 52 therefore reverses the operation performed by coder 20 (FIG. 6) when the originator enrolled, producing the originator's CPN, CPNO. CPNO is then applied as the key input to a coder 56, which receives the recipient's TIN, RTIN, as the data input.

In accordance with the embodiment just described, it is contemplated that security considerations may warrant revising the ROC from time to time independent of any transaction. Toward this end, CPN could be reconstituted from the current ROC and RN as in block 52. Next, a new RN is used with CPN to generate a revised ROC, making use of a coder in the same manner as coder 20 of FIG. 6. The user's new RN and ROC are stored and accessed, and CPN need only be reproduced at the bank where the user maintains an account.

In the same manner as coder 28 of FIG. 7, coder 56 therefore produces the joint key JK. JK is applied as the key input to an uncoder 58, which receives the VAN from check 32 as its data input. Uncoder 58 therefore reverses the coding operation performed by coder 30 of FIG. 7. If the information on the check has been unmodified, the coder 58 should therefore reproduce the information INFO from the check which was sought to be authenticated. In block 60, a comparison is made between the output of uncoder 58 and the information appearing on the check. Failure of this comparison is an indication that the check may have been modified after being issued, and the originator's bank notifies the recipient's bank that the check will not be honored. Alternatively, the joint key JK from the coder 56 can be used to code the information (INFO) from the check to generate a new VAN, which can then be compared with the VAN from the check to authenticate the check.

Should the comparison be favorable, this is an indication that the check is authentic and unmodified, and the originator's bank accesses the originator's account (block 61) to determine if the account is in order and has sufficient funds or credit to pay the check. The date of the check is determined to be acceptable. If the check control number does not appear in the originator's file as a previously cashed check, then the current check control number is saved to prevent fraudulent check reuse. The originator's bank generates a redeemed or redemption VAN (RVAN) in coder 54, using its bank key and the original VAN. RVAN is saved in the originator's file (block 55) and is recorded on the check (block 57). The originator's account is then debited. The originator's bank then authorizes the recipient's bank to pay the check. On the other hand, if originator's bank finds any irregularity in the check or in the originator's account, it will notify the recipient's bank that the check is dishonored.

The RVAN (and other RVAN's from other transactions) can be accessed from originators' files by banks and other financial institutions involved with processing checks to determine the status of checks. Thus, by creating and storing the RVANs in the originators' files, fraudulent reuse of checks is avoided.

At block 72 (FIG. 8A), the recipient's bank receives the originator's bank's instructions. It will then notify the recipient if the check has been dishonored. If the check has been honored, the recipient's account may be credited as in a deposit. Alternately, the recipient can receive payment immediately if he is at an appropriate terminal, such as an automatic teller machine.

Essentially, the check has cleared automatically, on-line, without further check handling or processing.

In a transaction where the user cashes his own personal check, the originator and recipient are one and the same. A VAN is created from a joint code which combines information associated with the user, such as the user's identification number (TIN or PAN) and the user's CPN, which is generated directly from a PIN entered by the user. When the VAN is authenticated, the joint code is derived by combining the user's identification number (TIN or PAN), and the user's true CPN, which is generated from the RN and ROC retrieved from the user's file, with the TIN (or PAN) serving as a file index.

As noted above, in FIG. 8A it is possible to use an unsecured link between the mixer 48 and the sorter 62 because CRNX and RNX, not CPNR, are transmitted from the mixer 48 to the sorter 62. However, a security problem still exists in using an unsecured line between the mixer 48 and the sorter 62 because the signal can be recorded and then played back later to attempt to fraudulently authenticate a fraudulent transaction. In an alternate embodiment of the present invention, an anti-duplication variable authentication number (ADVAN) is generated at the recipient's terminal by coding at least a transmission date and time with the CPNR by a coder (not shown). The ADVAN is then mixed with the CRNX and the RNX by the mixer 48 and sent to the remote bank CPU over the unsecured line to the sorter 62. At the remote bank CPU, the CPNR which is generated by the uncoder 70 is used to uncode the ADVAN to regenerate the transmission date and time. The signal received over the unsecured line is then authenticated by comparing the regenerated transmission date and time to a reception date and time (that is, the date and time at which the signal was received at the remote bank CPU). In this manner, the recipient and transaction are further authenticated.

According to another embodiment of the present invention, RNX is generated at both the recipient terminal and the remote bank CPU. To generate the RNX at the remote bank CPU, a random number generator is located at the remote bank CPU, wherein the random number generator at the remote bank CPU is similar to and synchronized with the random number generator 46 located at the recipient's terminal. Instead of transferring the RNX and the CRNX, only the CRNX is transferred over the unsecured line from the recipient's terminal to the remote bank CPU. At the remote bank CPU, the CPNR generated by the uncoder 70 is coded by the coder 66 with the RNX generated at the remote bank CPU to generate the CRNX. The generated CRNX is then compared by the comparator 64 with the CRNX transferred from the recipient's terminal to the remote bank CPU to authenticate the recipient and the signal received over the unsecured line. In this manner, the recipient and transaction are further authenticated.

According to another embodiment of the present invention, CRNX is never generated. Instead, the CPNR generated by the irreversible coder 42 is sent to the remote bank CPU over a secured line, rather than over an unsecured line. The CPNR generated by the uncoder 70 is then compared by a comparator (not shown) with the CPNR sent from the recipient's terminal to the remote bank CPU to authenticate the recipient. In this alternate embodiment, the random number generator 46, coder 44, mixer 48, sorter 62, and coder 66 are not required, although a secure line is required.

FIGS. 9-12 constitute a functional block diagram illustrating the present invention in a credential issuing and authentication system. The system involves the same three phases of operation as the check transaction system of FIGS. 6, 7, 8A and 8B. However, All users are enrolled by an authorized official who must be enrolled first. Accordingly, there are two enrollment processes which are somewhat different. The first one is enrollment of the official, and the second one is enrollment of a user prior to or at the time of issuing his credentials. It is contemplated that this system would be useful for all types of credentials and records; for example, motor vehicle registrations, social security cards, passports, birth certificates and all types of identification cards or personal storage media. This system would also be useful in protecting against unauthorized access to all types of records, as previously indicated.

FIG. 9 illustrates enrollment of the official. This can be accomplished at a terminal or computer which is in communication with a remote computer over a link which is assumed to be secure. The remote computer may, for example, be the central computer at the agency issuing the credential. At the remote computer, number generator 100 generates a random number which, at block 102, is compared to a current list of all assigned personal keys. If the random number does not correspond to an assigned personal key, then the random number is assigned as the personal key, PKO, of the official being enrolled. Alternatively, PKO can be selected at random, from a list of unused PKO's, and the list of available PKO's would thereby be diminished. In yet another alternative, PKO could be accessed from a counter, such as a pseudorandom or an ordinary sequential counter the output of which may be coded with a secret key. The size, or length, of PKO can be such as to provide a full size memory address or an offset or an index extension, to limit or enlarge the memory space wherein concealed files are stored. PKO is then transmitted over the secure link to the enrollment terminal.

At the terminal, the official enters his PIN and name and various other information required by the system. The name can be numerically coded by using a telephone type key pad. The PIN is applied to an irreversible coder 104, which produces his coded PIN CPNO. CPNO is applied as the key input to a coder 106, which receives PKO as the data input. The data output of coder 106 is the official's coded personal key, CPKO, which is applied as an input to mixer 107. The official's name code and TIN, OTIN, are also applied as inputs to mixer 107. CPKO represents a coded address since it is a coded representation of PKO.

The output of mixer 107 is transmitted back to the remote computer over the secure link. At the remote computer, sorter 109 separates the received signal into its component parts: CPKO, the official's name code, and OTIN. At block 108, CPKO and the official's name code are then saved (i.e., written) into File No. 1 assigned to the official with the official's TIN, OTIN, serving as a File No. 1 index. It is assumed that during the official's enrollment various other information will be provided by the official over the secure line and may be stored in his File No. 1. It should be noted that OTIN is not secret and, therefore, the location of File No. 1 and the contents of File No. 1 (including CPKO) are not secret.

At block 112, PKO is used as an index for File No. 2, which is also allocated to the enrolling official. The location of File No. 2 (and thus, the contents of File No. 2) is concealed, since PKO is secret and not stored anywhere in the system. The information or records which are stored in File No. 2 can be coded or uncoded. The memory space wherein concealed files are stored may be previously filled (or pre-loaded) with dummy or false information to make the contents and locations of authentic allocated files undistinguishable from the dummy files. The concealed File No. 2 can also be used to store the ROC and RN (or store only RN, since only RN is secret—ROC could be stored in a non-secret file, such as Official's File No. 1), as previously described in FIGS. 6, 7, 8A and 8B, to reconstitute a user's coded PIN, CPN. The concealed File No. 2 can also be used to store other secret information (not shown) associated with the official. An official's coded number, CNO, is generated at the output of coder 110, and is saved in File No. 2 at block 112. The key input to coder 110 is CPKO and the data input to coder 110 is PKO or an arbitrary predetermined number (APN). CNO represents coded authentication information because it is a coded representation of CPKO, and because it is used by the system to authenticate the official.

At coder 110, CPKO and PKO can be interchanged as the key and data inputs. However, the arrangement selected must then be used consistently in each phase of the operation of the system.

Those skilled in the art will appreciate that the present embodiment offers an additional level of security in that, not only is secret information unavailable to a person who does not know the related PK and PIN, but that person is even unable to determine the location of the file containing the information, and is unable to uncode the information contained therein.

FIG. 10 illustrates user enrollment. The user is enrolled by a previously enrolled official, who verifies the user's identity, based on acceptable documentation. Before the user can be enrolled, the official's identity and authority are preferably authenticated. The official operates the terminal, where he enters his PIN, and his TIN, OTIN, and the name code used during his enrollment, which was stored in his "File 1". OTIN is transmitted to the remote computer, where it is used as an index to access CPKO from the official's File No. 1, and CPKO is returned to the terminal. The official's PIN is applied to the irreversible coder 104, which produces CPNO. CPNO is applied as the key input to an uncoder 114, which receives CPKO as a data input over the secure link from the remote computer. It will be appreciated that uncoder 114 simply reverses the process of coder 106 of FIG. 9, therefore producing PKO. PKO is applied to a mixer 118, the other input to which is the official's name code. The output of mixer 118 is then transmitted to the remote computer.

At the remote computer, the signal transmitted from mixer 118 is received in a sorter 124, which separates out PKO, and the name code. The extracted PKO is utilized as an index to address the official's "File 2" whereby CNO is read. The CNO read from File No. 2 is compared against the CNO generated by coder 120, which has as its data input PKO which is extracted by sorter 124 and as its key input is CPKO read from "File 1". Should this comparison fail, the identity of the official is not authenticated and the enrollment of the user is aborted. Assuming that the comparison is successful, comparator 130 is then enabled. At block 130, the name code which is extracted from sorter 124 is compared against the name code read from the official's "File 1" (using OTIN as index). Should this comparison fail, the enrollment of the user is aborted. Should the comparison be successful, the official has been fully authenticated and the user's enrollment may proceed.

At the remote computer, number generator 100 generates a unique random number, which is assigned to the user as a personal address key, PKU. Alternately, PKU can be generated from a counter as previously described. As discussed below, PKU represents a predetermined secret address of a File No. 2 associated with the user. PKU is transmitted over the secure link to the enrollment terminal, where it is applied to the data input of coder 113.

The user operates the terminal and selects a PIN which he enters along with his TIN, UTIN. The user's PIN is applied to the irreversible coder 104, which produces the user's coded PIN, CPNU. CPNU is applied as a key input to coders 113 and 115. The output of coder 113 is the user's coded personal key, CPKU (which represents a coded address of the user's File No. 2), which is applied as a data input to coder 115. The output of coder 115 is the user's coded number, CNU, which is applied to the input of mixer 116. The user's TIN, UTIN and CPKU are also applied as inputs to mixer 116. The output of mixer 116 is transmitted back to the remote computer over the secure link. CNU represents coded authentication information because it is a coded representation of CPKU, and because it is used by the system to authenticate the user.

At the remote computer, sorter 119 separates the received signal into its component parts: CPKU, CNU and UTIN. At block 108, CPKU and CNU are saved (i.e., written) into File No. 1 assigned to the user, with the user's TIN, UTIN serving as a File No. 1 index. It should be noted that CPKU and CNU may be recorded on the user's credential when they are generated at the terminal. It should also be noted that UTIN is not secret, and therefore, the location and contents of the user's File No. 1 are not secret. It should further be noted that the official's CNO is stored in the official's secret File No. 2 (FIG. 9) while the user's CNU is stored in the user's non-secret File No. 1 (FIG. 10A), even though both CNO and CNU are used to authenticate the official and the user, respectively. These two different ways for storing CNO and CNU (as shown in FIGS. 9 and 10A) illustrate two embodiments of the present invention.

Figure 10B:
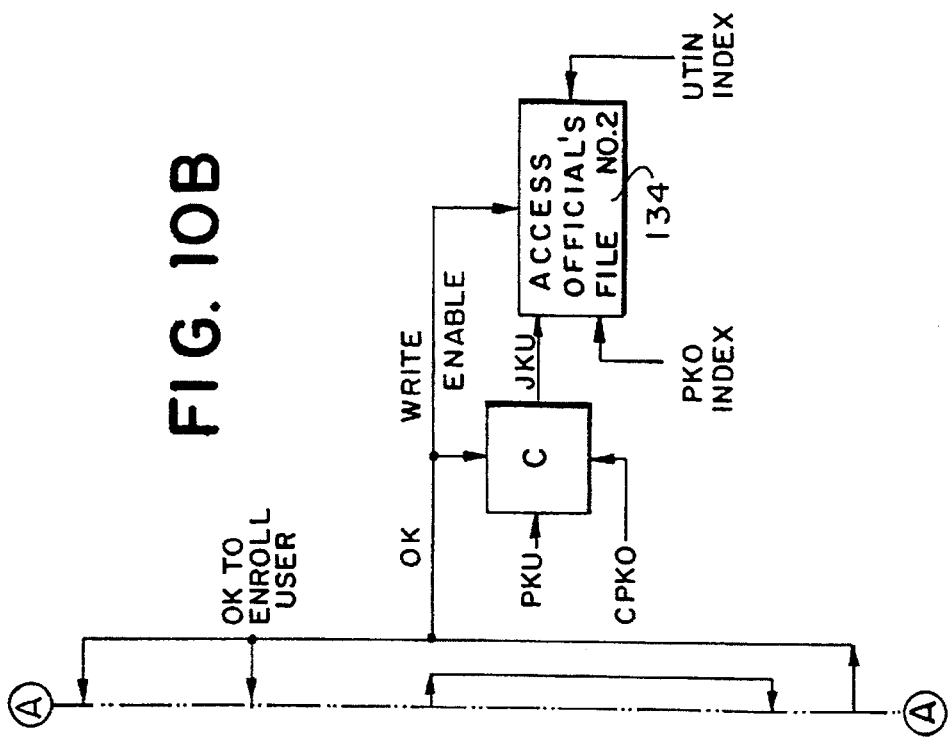

The user's PK, PKU (or an arbitrary predetermined number APN), is applied as the data input to a coder 132, which receives the official's CPKO as a key input. Coder 132 produces a joint key, JKU, which it will be appreciated, is determined by information related to the user and information related to the official. Using PKU as an address, the joint key is written into the user's "File 2" at block 112', and using PKO and UTIN as address indices, the Joint key JKU is written into the official's "File 2" at block 134 (FIG. 10B). These writes are enabled as a result of the success of the comparison occurring at block 130. Accordingly, the user's "File 2" will contain a joint key, and the official's "File 2" will contain a joint key for each user the official enrolls. Since the user's file 2 is addressed by PKU (which is secret), the location and contents of the user's file 2 are secret. At coder 132, when the joint key JKU is generated, CPK and PK can be interchanged as key and data inputs, or as to user and official inputs. However, the arrangement selected must then be used consistently.

Figure 11:
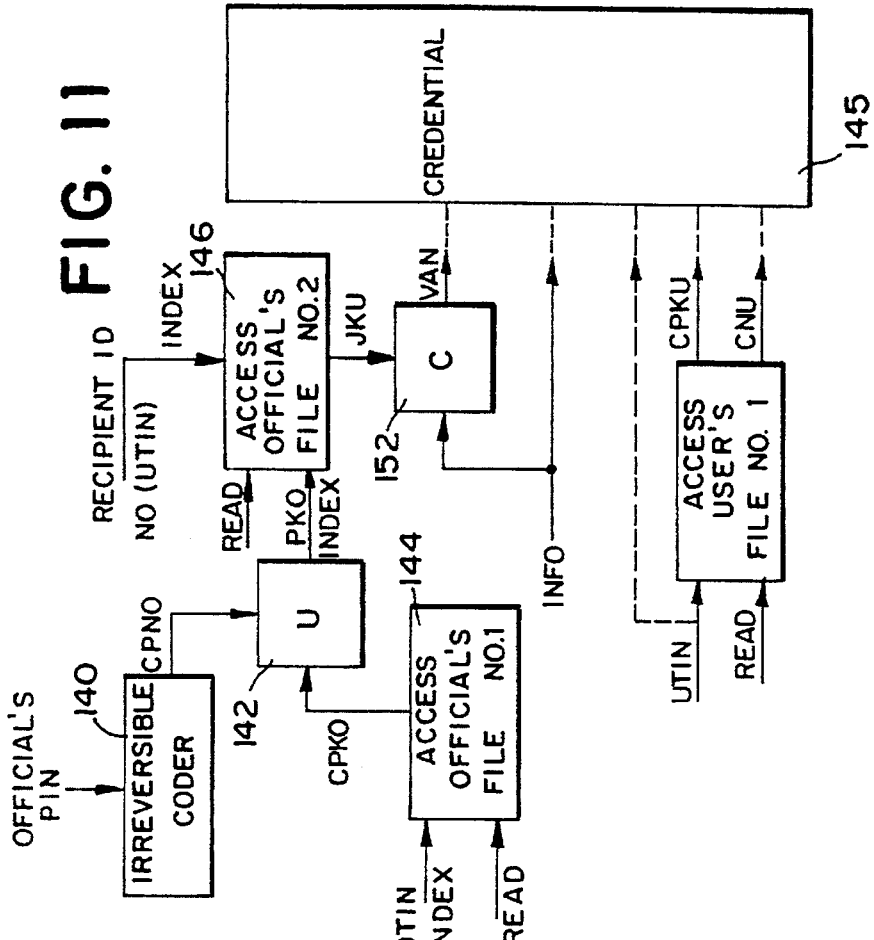

FIG. 11 illustrates issuance of the credential. This is shown separate from the user enrollment process of FIG. 10. However, in many instances, it would occur at the same time. In the preferred embodiment, this process is shown as occurring at the agency's computer, although it may be performed by the official from a terminal where he may communicate with the computer. It is assumed that the official has a credential printer or recorder which contains credential forms on which information is printed or recorded to produce the actual credential. However, it is also possible to create the credential by inserting information manually or on a typewriter, provided the necessary information derived by the system can be entered. The official enters the usual information (INFO) normally contained on a particular credential 145. The user's TIN may also be recorded on the credential. Alternately, the user's CPKU and CNU may be recorded on the credential, after being extracted from the user's File No. 1, with UTIN serving as a file index. If CPKU and CNU are recorded on the credential, they may be erased from the user's File No. 1. Alternatively, only CNU may be recorded on the credential, with CPKU remaining in File No. 1, or vice versa.

The issuing process continues with the official entering his PIN, which is applied to an irreversible coder 140 to produce his CPNO, which is applied as a key input to an uncoder 142. At block 144, the official's TIN, OTIN is utilized as an index to access the official's "File 1", so that CPKO may be read therefrom and applied as the input to uncoder 142. Uncoder 142 therefore performs the same process as uncoder 114 of FIG. 10 to produce PKO. At block 146, PKO and UTIN are utilized as address indices to access the official's "File 2" and JKU is read therefrom. The information INFO on the credential is applied as the data input to a coder 152 and JKU is applied as the key input, whereby coder 152 codes the INFO to produce a VAN, which is recorded on the credential. After recording the VAN on the credential, the joint key, JKU, may be erased from the official's File 2, where it was stored (or held in escrow or in trust), until the credential was issued. Alternately, the authentic JKU may be replaced with a false or dummy JK for security purposes. This completes the issuance of the credential 145. It should be noted that the joint key JKU stored in the official's File No. 2 can only be used in a transaction if a party exists with knowledge of the official's PIN, since this PIN is required to access the official's File No. 2 (at block 146). Thus, a person who does not have knowledge of the official's PIN (such as an unscrupulous person trying to issue a fraudulent credential) cannot legitimately issue a credential.

The VAN which is generated from information (INFO) recorded on the credential, or from information which is otherwise stored by the system, can include (coded) personal descriptive details to further identify the user (in addition to the user's PIN and TIN) in order to limit the use of the credential to the sole individual to whom it was issued (or sold). Thus, items such as bank cards, tickets, green cards, food stamps, ballots, travel checks, FAX messages, etc., can be protected and used solely by the individuals to whom they were issued. Also, the use of the credential may be enlarged to include a group, such as a family, by coding such information into the VAN.

Figure 12A:
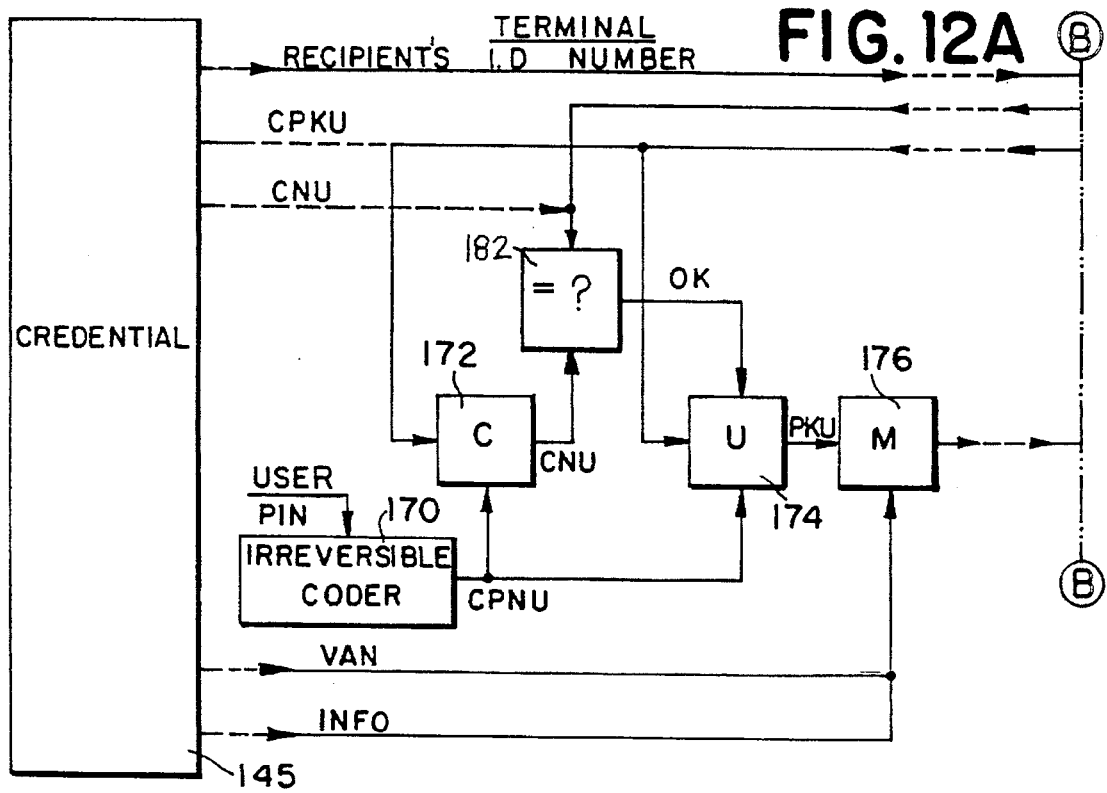
Figure 12B:
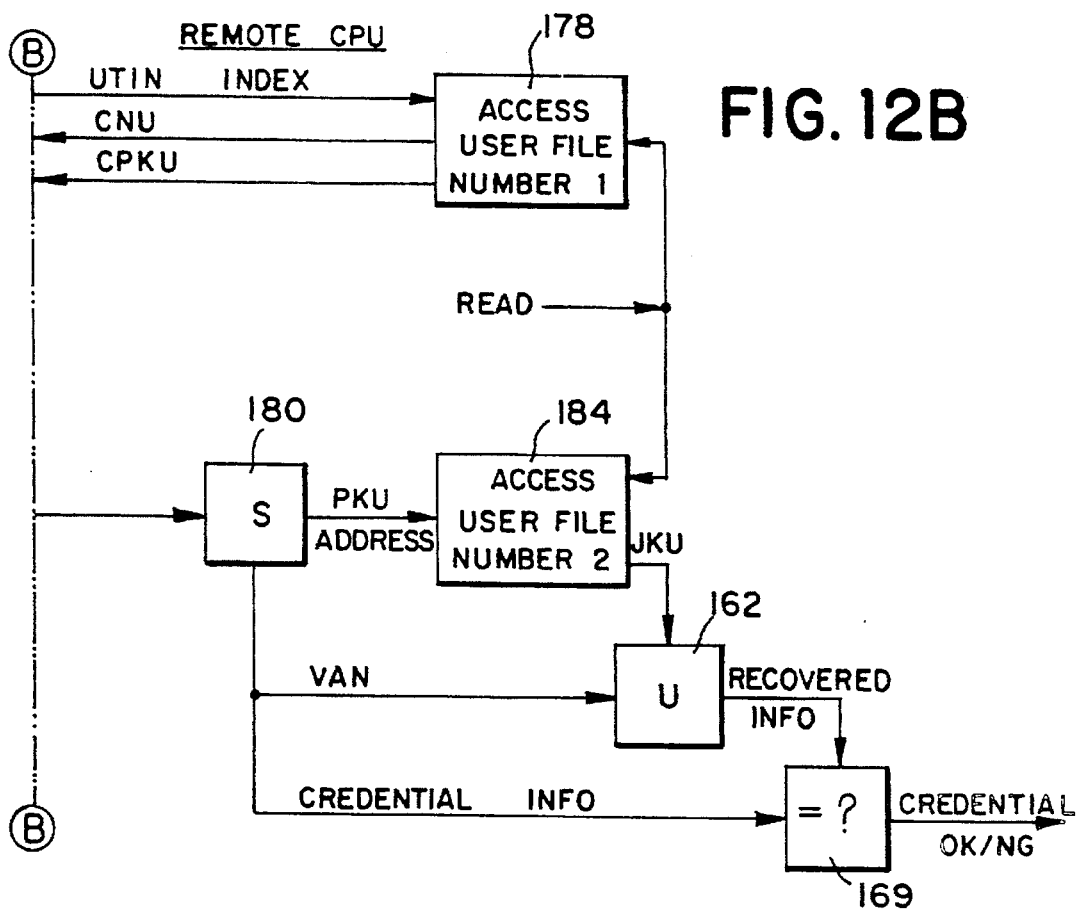

FIG. 12 illustrates the authentication of an issued credential. This is preferably performed at a terminal provided for that purpose. The terminal includes a reading device for the credential 145 and an input device, such as a keypad for the user. The information could, however, be read from the credential and keyed in by hand. The terminal communicates with the remote processor via a preferably secure link.

As part of the credential authentication process, the identity of the user is authenticated. This requires that the user enter certain information at the terminal, including a PIN and user's TIN, UTIN, which is transmitted to the remote computer, which returns CPKU and CNU (box 178) via a secure data link. Alternatively, CPKU and CNU could have been recorded on the credential (or on some other item in the possession of the user, such as a card having a magnetic stripe for storing data) and inputted directly into the terminal. The PIN is applied to the irreversible coder 170 which produces CPNU. CPNU is applied as the key input to coder 172 and uncoder 174. Coder 172 receives CPKU as a data input. It should be noted that coder 172 performs in the same manner as coder 115, which produced CNU at its output during the user's enrollment. The output of coder 172 is applied as an input to the comparator at block 182, which also has as an input the CNU extracted from the user's File No. 1 (or inputted from the user's credential).

Should this comparison fail, the identity of the user is not authenticated, and the credential authentication is aborted. Assuming the comparison is successful, the user is identified, and the credential authentication, with access to the hidden File No. 2, ensues. The favorable output from comparator 182 enables uncoder 174. The data input to uncoder 174 is the user's CPKU. The key input to uncoder 174 is the user's CPNU, as already explained. It will be appreciated that uncoder 174 simply reverses the process of coder 113 of FIG. 10, therefore producing PKU. PKU is applied to a mixer 176 which also receives the VAN and INFO of the credential. The output of mixer 176 is then transmitted to the remote computer over the secure link.

At the remote computer, UTIN is utilized as an index to access the user's "File 1" at block 178. This permits reading of CPKU and CNU from the file, whereby CPKU and CNU were transmitted back to the user's terminal. At the remote computer, the signal transmitted from mixer 176 is received in sorter 180, which separates out PKU, VAN and INFO. The extracted PKU is utilized to address the user's "File No. 2" at block 184 whereby JKU is read. It will be appreciated that the user's File No. 2 has been accessed by an authorized user without reference to, or use of, information stored in the file. The VAN extracted from sorter 180 is applied as a data input to an uncoder 162, which receives the joint key JKU extracted from the user's "File 2" at block 184. It will be appreciated that uncoder 162 therefore reverses the process performed by coder 152 of FIG. 11. Assuming the VAN on the credential is the same one as originally recorded, uncoder 162 will have produced the recovered INFO which should be the same as the actual INFO recorded on the credential.

At block 169, the INFO from the credential is compared to the INFO recovered from uncoder 162. Should the comparison fail, this is an indication that INFO on the credential has been modified, and the credential is indicated as not being authentic. Should the comparison be successful, this is an indication that INFO is accurate, and the authenticity of the credential is confined. Alternatively, the credential information from the credential is coded using the JKU from the user's File No. 2 to generate a new VAN, which is compared with the VAN from the credential to authenticate the credential.

In order to enhance the security of this system, it would be desirable to make unassigned areas of memory indistinguishable from those utilized to store information for the "File 1" and "File 2" information. This is accomplished by pre-storing pseudo-information in unused memory allocated as hidden memory space. This pseudo-information constitutes random information arranged in the same format as actual files. This prevents an intruder from searching memory for structures that look like actual information files and using the uncovered information to work backwards to breech security.

FIGS. 13A–13E, when arranged as shown in FIG. 14, constitute a functional block diagram illustrating further aspects of the check transaction system of FIGS. 6, 7, 8A and 8B. Specifically, these figures illustrate a three-party check transaction, with each of the participants and the fidelity of the information on the check being authenticated, the check being automatically cleared, and the funds of the participants being immediately credited or debited, all of these processes being performed on-line. The participating parties in this transaction are the check originator, whose account is to be debited; the check recipient to whom the check is drawn; and the check redeemer, who is cashing the check for the recipient or accepting it in payment for goods or services, and whose account is to be credited. In addition, the banks for each of these participants will also be participating in the transaction, and the messages generated by these banks will be authenticated. It is assumed that any individual or bank participating in the system will have enrolled as illustrated in FIG. 6. In addition, it is assumed that a check used in the system is generated in the manner illustrated in FIG. 7.

Figure 13A:
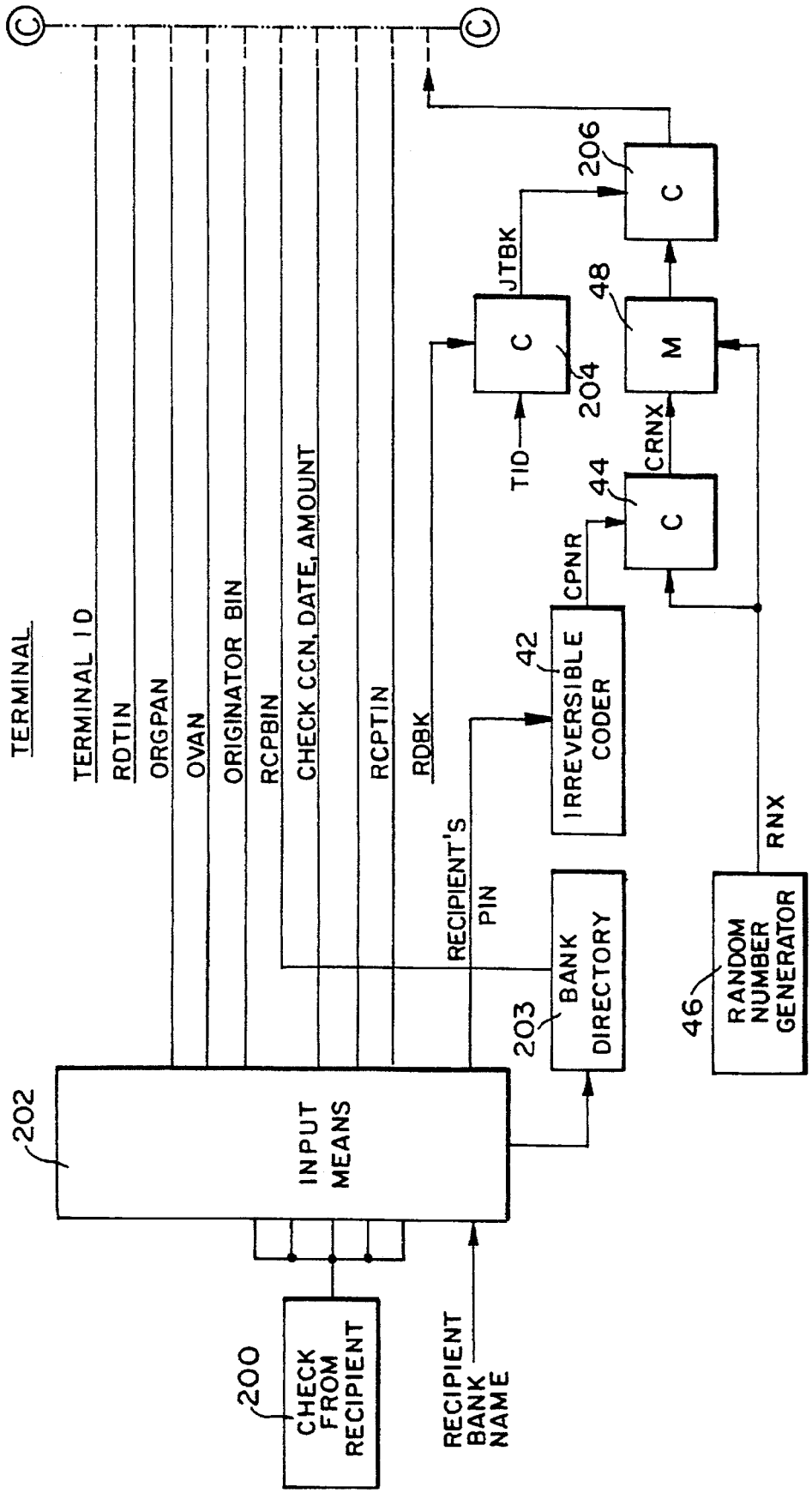
Figure 13B:
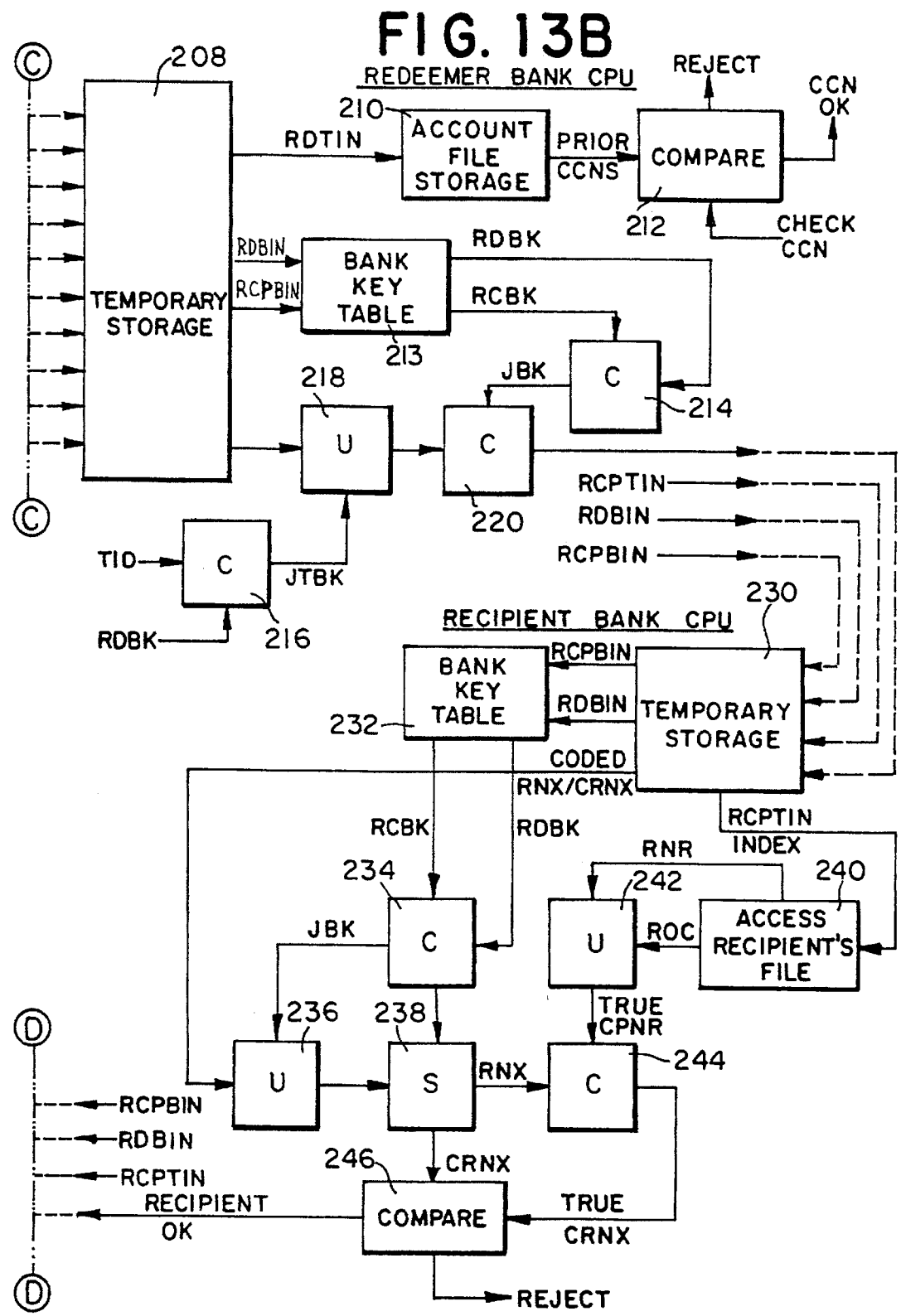

Referring first to FIG. 13A, the recipient of the originator's check has presented the check to the redeemer (block 200). The recipient and the redeemer are at a terminal which includes appropriate input means 202. Preferably, the input means includes a check reader and a keypad for each of them. However, in the absence of a check reader, it is also possible to key in information from the face of the check. The check is examined to determine if it contains a redemption VAN from a previous transaction. The presence of a redemption VAN is an indication that the check was used previously, and it will not be honored. If a redemption VAN is not present, then the transaction can proceed. It is assumed that the redeemer's bank identification number (RDBIN), and TIN are stored in the terminal, otherwise the redeemer keys in his bank's name and TIN, and the recipient keys in his TIN, PIN and bank's name. A bank directory is addressed at block 203 to produce the recipient bank's identification number (RCPBIN). The recipient's PIN is applied to an irreversible coder 42, which produces his CPNR. Irreversible coder 42, coder 44, random number generator 46, and mixer 48 are the same components illustrated in FIG. 8A and cooperate in the same manner to produce RNX, CRNX, in a mixed form at the output of mixer 48.

The terminal has available to it the redeemer's bank key (RDBK), which is applied to the key input of a coder 204, the data input to which is the terminal ID (TID), which is generated by the terminal. Coder 204 then produces a joint terminal bank key (JTBK), which is applied as the key input to a coder 206, the data input to which is the output of mixer 48. The mixer output is therefore coded with a joint key JTBK which has been generated on the basis of information related to the redeemer's bank identity and the terminal identity.

The output of coder 206 and the information from input means 202, and the recipient's TIN, RCPTIN, and the recipient's bank ID number, RCPBIN, are then transmitted to the computer at the redeemer's bank. At the redeemer's bank (FIG. 13B), all of the received information is placed in temporary storage (block 208).

The redeemer's TIN, RDTIN, (originally stored in the terminal, or keyed in by the redeemer), is then utilized as an index to access his account file, at block 210.

The check control number (CCN) of the present check is then compared to the CCN's stored in the redeemer's file during previous transactions (block 212), and the transaction is terminated if the present CCN matches that of a previously processed check. If the CCN of the present check is not a duplicate, processing continues.

RDBIN, and RCPBIN are utilized as indices to access a bank key table (block 213), which produces the redeemer's bank key RDBK, and the recipient's bank key RCBK, which are applied as the data and key inputs, respectively, to a coder 214. The coder 214 then produces a joint bank key JBK, which is derived from information related to the identity of the redeemer's bank and the identity of the recipient's bank.

The terminal identification (TID) is input to a coder 216, which has as a key input RDBK. In the same manner as coder 204, coder 216 therefore produces JTBK, which is applied as a key input to an uncoder 218. The data input to uncoder 218 is the information in temporary storage 208 which was originally received from coder 206. Coder 218 therefore reverses the process performed by coder 206, yielding the output of mixer 48, which is applied as a data input to a coder 220. The key input to coder 220 is JBK, so that the output of mixer 48 is now coded with the joint bank key JBK. The output of coder 220 is then transmitted in a message to the recipient's bank, along with RCPTIN, RDBIN, and RCPBIN.

At the recipient's bank, the received information is saved in temporary storage 230. RCPBIN and RDBIN are then applied to a bank key table (block 232), to yield RCBK and RDBK, which are applied as the key and data inputs, respectively, to a coder 234. In the same manner as coder 214, coder 234 therefore yields the joint bank key JBK, which is applied as a key input to uncoder 236. The data input to this uncoder 236 is the coded combination of RNX and CRNX produced by coder 220. Uncoder 236 therefore reverses the process of coder 220, yielding the mixture of RNX and CRNX as an output. This mixture is applied as an input to a sorter 238, to recover RNX and CRNX.

The recipient's TIN, RCPTIN, is utilized as an index to access the recipient's file at block 240 and read therefrom the random number, RNR, and his ROC, which are applied as the key and data inputs, respectively, to an uncoder 242. In the same manner as uncoder 70 of FIG. 8A, uncoder 242 therefore derives the true CPNR, which is applied as a key input to a coder 244, which receives RNX as a data input. The data output of coder 244 is therefore the true CRNX.

At block 246, this true CRNX is compared to the CRNX derived from sorter 238. If this comparison is favorable, the recipient's identity is confirmed, and processing may proceed. Otherwise, processing is terminated, with the originator's check being dishonored, because the recipient has not been properly authenticated. The recipient's bank then transmits a message to the redeemer's bank, informing it whether or not the recipient has been authenticated. If the recipient has not been authenticated, the redeemer's terminal is notified, and processing will terminate.

Assuming that the recipient has been authenticated, the recipient's bank message includes various information which is temporarily stored by the redeemer's bank (block 250 of FIG. 13C). At block 252, the originator's bank identification number ORBIN, which was read from the check, and the redeemer's bank identification number RDBIN are applied as indices to a bank key table to recover bank keys for these banks, OBK and RDBK, respectively. These keys are applied to a coder 254 to produce a joint bank key JBK', which is therefore dependent upon information related to the originator's bank and the information related to the redeemer's bank. JBK' is applied to the key input of a coder 256, which receives the original VAN, ORAN, (from the check) as a data input. The output of coder 256 is a redeemer's bank RDBVAN, which is transmitted to the originator's bank, along with various transaction information and the information from the check. RDBVAN serves to authenticate the communication between the banks.

Figure 13D:
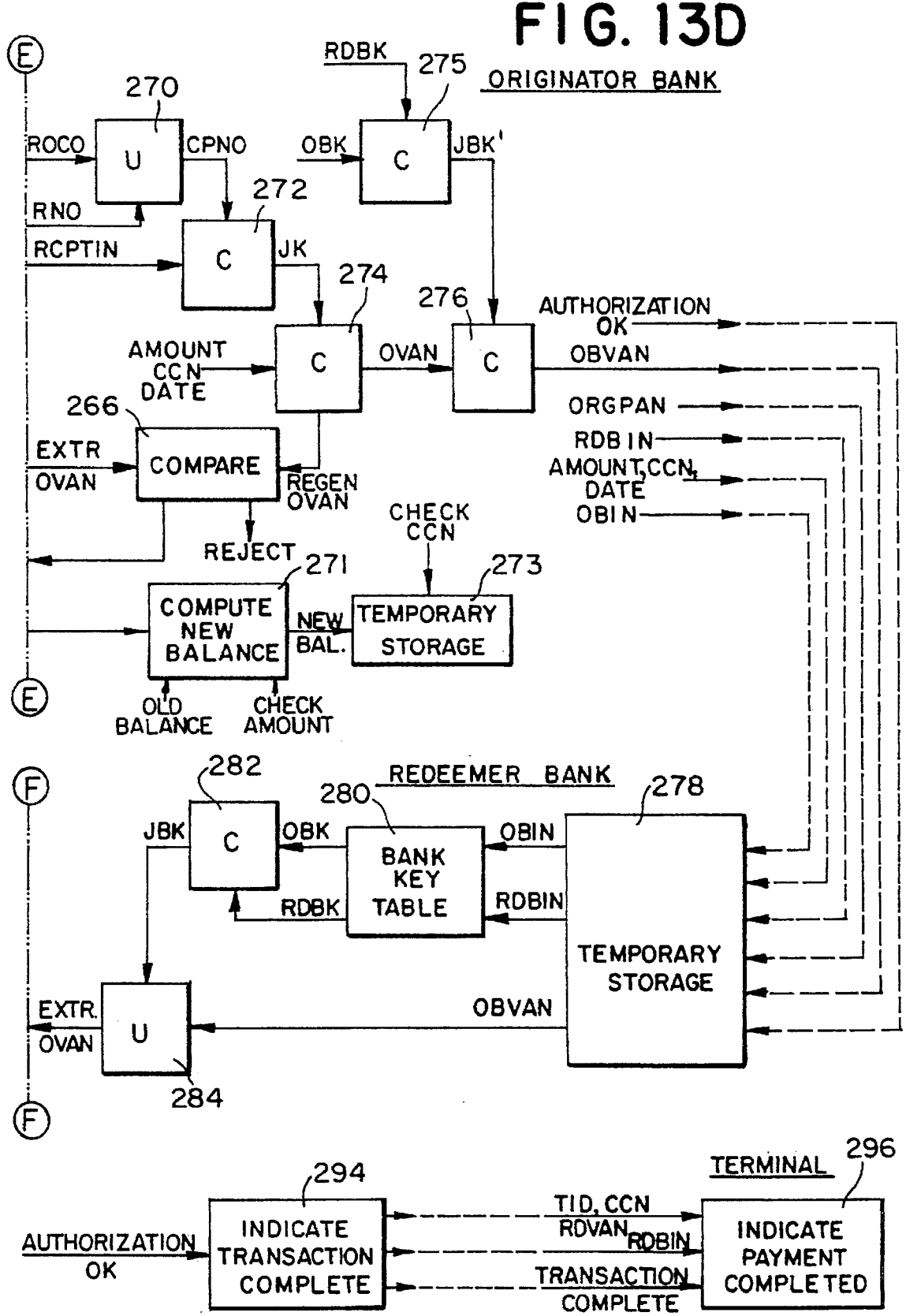

At the originator's bank, the received information is temporarily stored at block 258. ORBIN and RDBIN are then utilized to reference a bank key table at block 260, whereby OBK and RDBK are extracted in the same manner as in block 252. The joint key JBK' is then generated by means of a coder 262 in the same manner as coder 254. JBK' is then applied as the key input to an uncoder 264, which receives RDBVAN as a data input. This uncoder 264 therefore reverses the process performed by coder 256 and produces an extracted OVAN, which is applied to a comparator 266 (as shown in FIG. 13D).

The originator's personal account number ORGPAN which originally appeared on the check is utilized as an index to access the originator's account file at block 268 of FIG. 13C. This provides access to various information about the originator's account including the balance and a list of prior check control numbers (CCN's), and in addition, provides access to his revisable owner code ROCO and random number RNO, which are applied as the data and key inputs to an uncoder, to produce the originator's coded pin CPNO. CPNO is then applied as the key input to a coder 272 (FIG. 13D) which receives the recipient's TIN, RCPTIN, as a data input. The output of coder 272 is the joint key JK, which is applied as the key input to a coder 274, which receives the check information as a data input. It will be appreciated that coders 272 and 274 regenerate the original VAN, OVAN, from the check in the same manner as coders 28 and 30 of FIG. 7. This regenerated VAN is then compared to the extracted VAN at block 266. If this comparison fails, it is an indication that the check information may have been tampered with and the originator's bank informs the redeemer's bank that the check will be dishonored. On the other hand, if the comparison succeeds, the process continues.

The originator's bank then performs a series of computations, including determining Whether the CCN of the check is proper (i.e., has not been used before) and whether the originator has a sufficient balance in his account (or credit) to cover the check, and whether the date of the check is acceptable. In the case of any defects, the check will be dishonored and the process will terminate. Assuming that everything is in order, modification of the originator's account is approved, and a record of the check created at block 271, with the new information being added to temporary storage at block 273. Coders 275 and 276 are then utilized to encode the original VAN, OVAN, into an originator's bank VAN OBVAN. Various information about the transaction, and authorization to credit the redeemer's account are then transmitted is a message to the redeemer's bank.

At the redeemer's bank, all of the received information is stored in temporary storage at block 278. At block 280, coder 282 and uncoder 284, steps are performed to extract OVAN from OBVAN in a manner which is similar to that which was done in block 260, coder 262 and uncoder 264. This extracted OVAN is then applied to a comparator 286 of FIG. 13E, which receives as an additional input the stored OVAN from the check presented by the recipient. If this comparison fails, the process has not been authenticated, and the originator's bank will be notified. On the other hand, if the comparison succeeds, this is an indication that full authentication of the entire process and all parties has occurred and that the message received from the originator's bank is authentic.

Processing then continues by accessing the redeemer's account at block 288, computing a new balance at block 290 and updating the redeemer's account. The redeemer's bank then transmits a message back to the originator's bank, informing it that the redeemer's account has been credited. This information is saved at the originator's bank in temporary storage at block 291. The originator's bank then accesses the originator's account file using his personal account number ORGPAN as an index, and updates his account with the information that was placed in temporary storage at block 273 (FIG. 13D).

The redeemer's bank also communicates with the terminal at which the check was presented (block 294 of FIG. 13D), and informs it that the transaction has been satisfactorily completed and that the recipient may receive payment in the form of cash, goods or services (block 296). The terminal prints the redemption VAN (RDBVAN) on the check.

Although various embodiments of the present invention have been described herein as useful for particular types of transactions, those skilled in the art will appreciate that they actually have universal utility. For example, the last embodiment (depicted in FIGS. 13A–13E) was described as useful in a check transaction system, but it will be appreciated that it would also be useful in a bill payment system as well as a paperless/cashless system (as further described below).

Figure 15A:
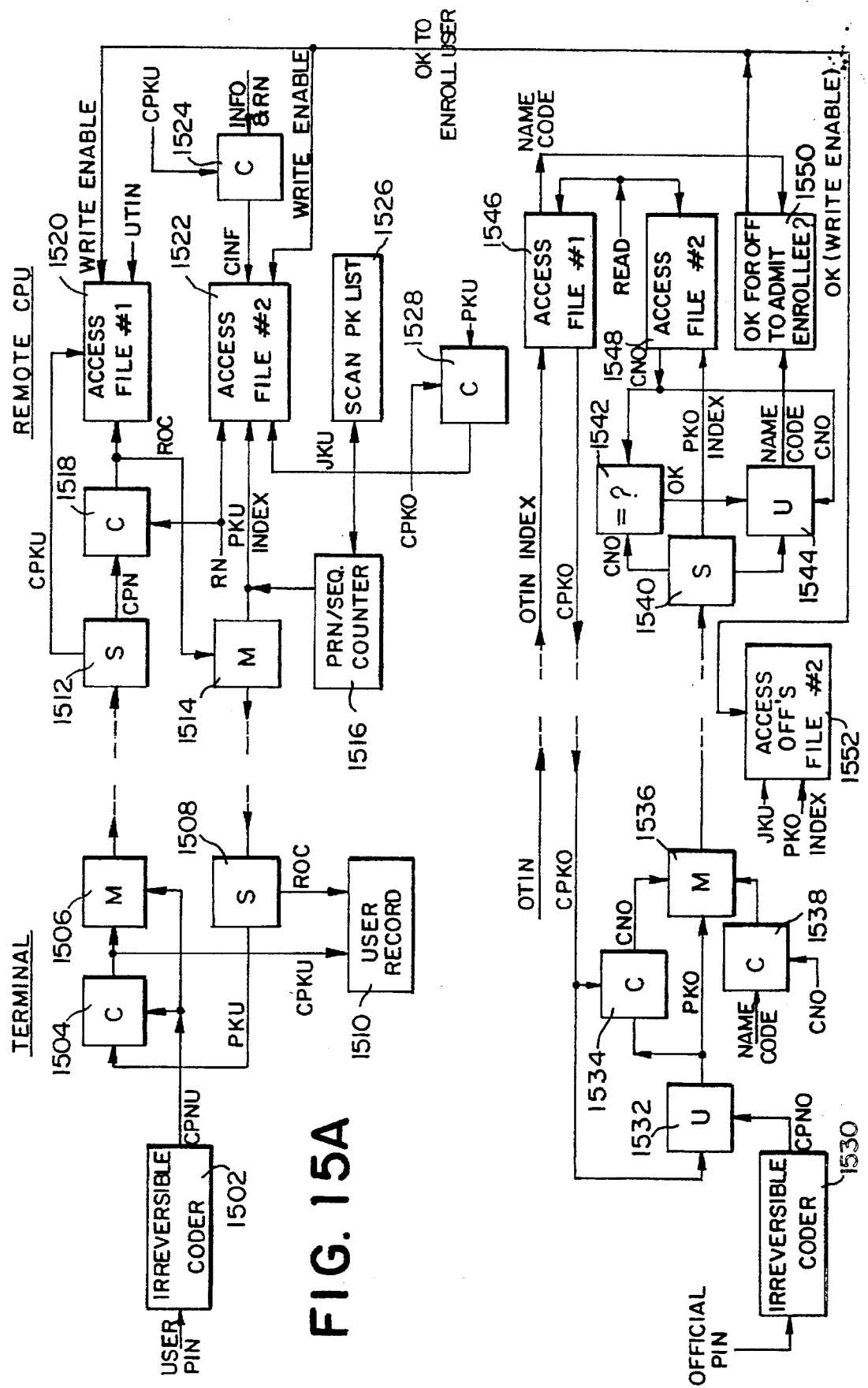
FIGS. 15A–15C are functional block diagrams of a credential issuing and authentication system according to an alternate embodiment of the present invention.
Figure 15B:
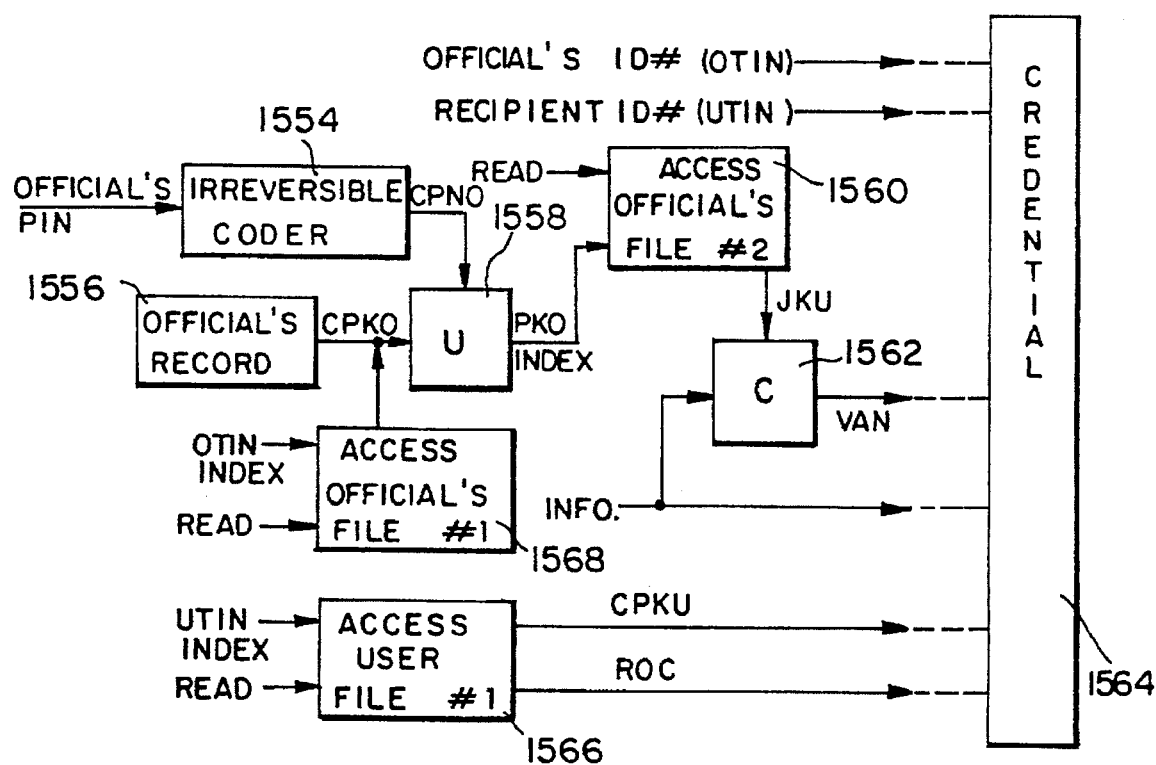
Figure 15C:
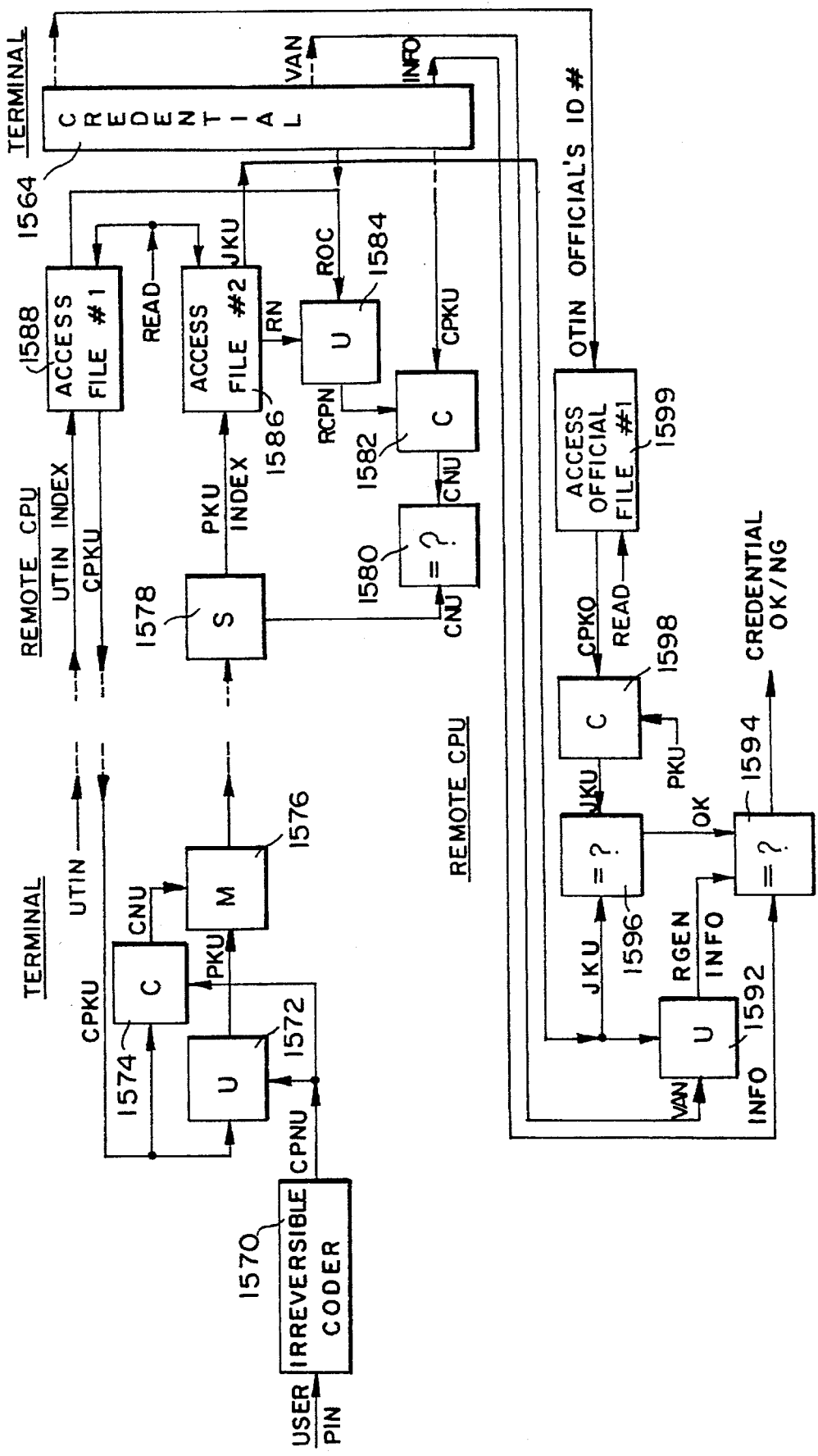

FIGS. 15A, 15B and 15C are functional block diagrams of a credential issuing and authentication system according to an alternate embodiment of the present invention, wherein the alternate embodiment includes many of the features of the embodiments depicted in FIGS. 6–8 and FIGS. 9–12. For example, the alternate embodiment of FIGS. 15A–15C include steps for enrolling an official, enrolling a user, issuing a credential, and authenticating the credential. FIG.

15A illustrates user enrollment, FIG. 15B illustrates issuance of a credential, and FIG. 15C illustrates the authentication of an issued credential. In the alternate embodiment of FIGS. 15A–15C, enrollment of the official is the same as shown in FIG. 9 and, therefore, shall not be discussed further.

Referring to FIG. 15A, a user is enrolled by a previously enrolled official who verifies the user's identity, based on acceptable documentation. Before the user can be enrolled, the official's identity and authority must be authenticated. The official operates a terminal, where he enters his PIN and his TIN, OTIN, and the name code used during his enrollment, which was stored in his File No. 1. OTIN is transmitted to the remote computer, where it is used as an index or address to access the official's File No. 1 and retrieve CPKO (block 1546). CPKO is returned to the terminal.

The official's PIN is applied to irreversible coder 1530, which produces CPNO. CPNO is applied as the key input to an uncoder 1532, which receives CPKO as a data input from the remote computer, and which uncodes CPKO to generate PKO. CPKO is also applied as a key input to a coder 1534, which receives PKO as an input. The coder 1534 codes PKO using CPKO as the key input to generate a coded number for the official (CNO), which represents coded authentication information. Another coder 1538 codes the official's name code using CNO as a key input to generate a coded name code. A mixer 1536 mixes the coded name code, PKO, and CNO and transmits the mixed signal to the sorter 1540 at the remote computer over preferably a secure link.

At the remote computer, the signal transmitted from mixer 1536 is received by the sorter 1540, which separates out PKO, CNO, and the coded name code. PKO is applied as an index (or address) to access the official's File No. 2 and to thereby retrieve CNO, which was previously stored in the official's File No. 2 during the enrollment of the official (see FIG. 9). The CNO transmitted from the terminal and the CNO retrieved from File No. 2 are then compared in a comparator 1542. If the comparison fails, the identify of the official is not authenticated and the enrollment of the user is aborted. Assuming that the comparison is successful, the comparator 1542 is enabled and sends a signal to an uncoder 1544. The uncoder 1544 then uncodes the coded name code using the CNO retrieved from the official's File No. 2 to regenerate the name code. The name code is also accessed from File No. 1 and then compared at 1550. If the comparison fails, the identify of the official is not authenticated and the enrollment of the user is aborted. Assuming that the comparison is successful, the comparator 1550 sends an authentication signal ("okay to enroll user") and user enrollment begins. It should be noted that the "okay to enroll user" signal is applied as a write enabled to the official's File No. 2 at 1552 to save a joint key JKU therein (described below).

At the remote computer, number generator 1516 generates a unique random number (as discussed above), which is assigned to the user as a secret predetermined address or key, PKU. PKU is transmitted over a secured link to the enrollment terminal, where it is applied to the data input of a coder 1504.

The user operates a terminal and selects a PIN which he enters along with his TIN, UTIN. The user's PIN is applied to irreversible coder 1502 which produces the user's coded PIN, CPNU. CPNU is applied as a key input to coder 1504. The output of the coder 1504 is the user's coded predetermined address or key, CPKU. CPKU may be stored in a user record (at block 1510). A mixer 1506 mixes CPNU and CPKU and transmits the mixed signal to the remote CPU.

At the remote computer, sorter 1512 separates the received signal into its component parts CPKU and CPN. At the remote computer, a random number RN is generated (as discussed above) and applied as a key input to coder 1518. The coder 1518 also receives CPN as an input and thereby generates a revisable owner code (ROC). ROC is stored in the user's File No. 1 (at block 1520), wherein the user's File No. 1 is accessed (or addressed) using UTIN. CPKU is also stored in the user's File No. 1 (at block 1520).

PKU is applied as an index or address to the user's File No. 2 in order to store RN (at block 1522). PKU is secret in the system and, therefore, the location and contents of the user's File No. 2 (including RN) is secret. Additional information may be coded in a coder 1524 using CPKU as a key input to generate coded information which is also stored in the user's File No. 2. The information which is coded using CPKU in the coder 1524 may include the secret information RN.

PKU is applied as an input to coder 1528, which also receives CPKO as a key input. The coder 1528 generates a user joint key (JKU) which is stored in the user's File No. 2. JKU is also stored in the official's File No. 2 (at block 1552).

It should be noted that the storage and handling of RN and ROC in the embodiment shown in FIG. 15A is different from the storage and handling of RN and ROC shown in FIG. 6. In FIG. 6, the file in which RN and ROC are stored is generally non-secret because it is indexed (or addressed) by generally non-secret user information (such as the user's TIN). However, in the embodiment shown in FIG. 15A, the non-secret ROC is stored in the user's File No. 1, which is non-secret, and the secret RN is stored in the user's File No. 2, which is secret (since it is accessed or addressed using the secret PKU). Therefore, the embodiment of 15A includes an additional level of security and protection over the embodiment shown in FIG. 6.

FIG. 15B illustrates issuance of a credential according to the alternate embodiment of the present invention. The issuance of credential in the alternate embodiment is essentially the same as the issuance of credentials in the previous embodiment shown in FIG. 11. Note, however, that it is possible to record the ROC retrieved from the user File No. 1 on the credential 1564 since the ROC is public (although the ROC could also have been recorded on the credential in the previous embodiment).

FIG. 15C illustrates the authentication of an issued credential. This is preferably performed at a terminal provided for that purpose. The terminal includes a reading device for the credential 1564 and an input device, such as a keypad, for the user. The information from the credential 1564 could, however, be keyed in by hand. The terminal communicates with the remote processor via a preferably secured link. As part of the credential authentication process, the identity of the user is authenticated. Specifically, the user enters his PIN which is applied as an input to irreversible coder 1570, which generates a coded PIN (CPNU). The user also enters his TIN (UTIN), which is used to access the user File No. 1 (at block 1588) and retrieve CPKU, which is transmitted from the remote CPU to the terminal. CPKU is applied as an input to coder 1574, which also receives CPNU as a key input. The coder 1574 generates a coded number CNU, which represents coded authentication information. CPKU is also applied as an input to uncoder 1572, which also receives CPNU as a key input. The uncoder 1572 uncodes CPKU to regenerate PKU. Both CNU and PKU are mixed by mixer 1576 and sent to the sorter 1578 at the remote CPU.

At the remote CPU, the sorter 1578 separates the signal into its component parts PKU and CNU. PKU is applied as an index into the user's File No. 2 in order to retrieve the secret information RN. UTIN is applied as an index to the user's File No. 1 to retrieve the non-secret revisable owner code (ROC). ROC is applied as an input to uncoder 1584, and the secret information RN is applied as a key input to uncoder 1584. The uncoder 1584 thereby uncodes ROC using RN in order to regenerate CPNU as RCPN, which is applied as a key input at coder 1582. CPKU, which is read from the credential 1564, is applied as an input to coder 1582. The coder 1582 codes CPKU using RCPN as a key input in order to generate a coded number CNU. The generated coded number CNU is compared at the comparator 1580 to the coded number CNU received from the terminal. If the comparison fails, authentication of the user aborts. However, if the comparison is successful, the user is authenticated and the process continues by authenticating the credential 1564.

The credential 1564 is authenticated by reading the official's ID number OTIN from the credential and using OTIN as an index in order to access the official's File No. 1 and read CPKO (block 1599). CPKO is applied as an input to coder 1598 which also receives PKU as a key input. The coder 1598 codes CPKO using PKU in order to regenerate the user joint key JKU. JKU is also read from the user's File No. 2 using PKU as an index and then applied to a comparator 1596. The comparator 1596 compares the JKU which was retrieved from the user's File No. 2 and the JKU which was generated by the coder 1598. If the comparison fails, then authentication of the credential aborts. However, if the comparison is successful, the comparator 1596 is enabled and sends an okay signal to a comparator 1594.

The JKU retrieved from the user's File No. 2 at 1586 is applied to an uncoder 1592, which also receives as an input the VAN which was read from the credential 1564. The uncoder 1592 uncodes the VAN in order to regenerate INFO. The regenerated INFO is applied as an input to the comparator 1594, which also receives the INFO read from the credential 1564. The comparator 1594 compares the regenerated INFO and the INFO from the credential and if the comparison is successful, the credential is authenticated. Otherwise, the credential is not authenticated.

As noted above, in FIG. 15C, the transmission link between the mixer 1576 and the sorter 1578 is preferably secured since using an unsecured link would present a potential security problem. For example, the signal from the mixer 1576 could be recorded and then transmitted to the sorter 1578 at a later date in order to attempt to fraudulently authenticate a user and a credential. In accordance with an alternate embodiment of the present invention, an anti-duplication variable authentication number (ADVAN) is generated at the terminal by coding at least a transmission date and a time with the CPNU. The ADVAN is then mixed with the CNU and the PKU at the mixer 1576 and sent to the sorter 1578 at the remote CPU over an unsecured link. At the remote CPU, the received ADVAN is uncoded using the derived RCPN to regenerate the transmission date and the time. The regenerated transmission date and time are then compared to a reception date and time (that is, the date and time at which the signal was received at the sorter 1578) and if the comparison is successful, the information transmitted over the transmission medium between the mixer 1576 and the sorter 1578 is authenticated. In this manner, the user and credential are further authenticated.

Alternatively, a semi-random number (not shown) is generated at the terminal using a counter or other random number generator (not shown). The semi-random number is coded using the CPNU to generate a coded semi-random number. The coded semi-random number is then transmitted along with CNU and PKU to the remote CPU over an unsecured medium. At the remote CPU, the coded semi-random number is uncoded using RCPN to regenerate the semi-random number. A second semi-random number is then generated at the remote CPU using another counter or random number generator (not shown) which is generally synchronized with the counter (not shown) at the terminal. The communication medium between the mixer 1576 and the sorter 1578 is then authenticated by comparing at the remote CPU the regenerated semi-random number to the second semi-random number which was generated at the remote CPU. If the comparison is successful, then the information transmitted over the communication medium between the mixer 1576 and the sorter 1578 is authenticated. In this manner, the user and credential are further authenticated.

As described above, the predetermined secret address PKU is coded to generate the coded secret address CPKU. According to an alternate embodiment, PKU comprises one or more components which are combinable to form the predetermined secret address PKU. In this alternative embodiment, only one of the components of the PKU is transmitted from the remote CPU to the terminal. The coder 1504 (FIG. 15A) codes this one component of the PKU to generate CPKU. Therefore, in this alternate embodiment, CPKU represents a coded portion of the PKU. Then, to access the user's File No. 2, the CPKU is uncoded as described above to regenerate the portion of the PKU. This PKU portion is combined with the other portions of the PKU to regenerate the PKU, which is then used to access the user's File No. 2. The other portions of the PKU may be stored throughout the system, such as in the operating system, in the executive program, in files, etc.

Figure 16:
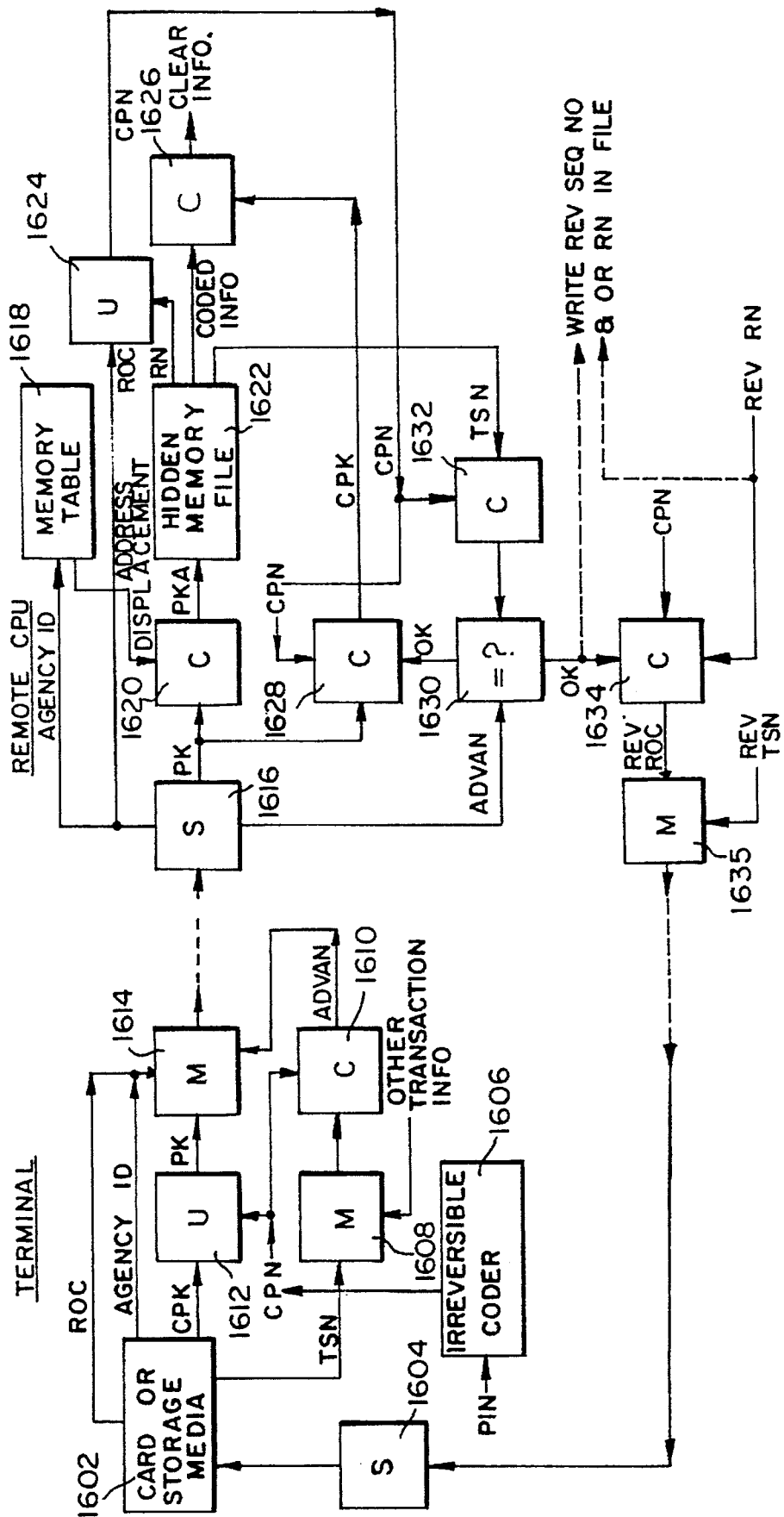
FIG. 16 is a functional block diagram of a system for authenticating a party and for authorizing access to a secret file associated with the party according to an alternate embodiment of the present invention.

FIG. 16 is a functional block diagram of a system for authenticating the identity of a party and for authorizing access to a party's hidden (or secret) file according to an alternate embodiment of the present invention. The party's hidden file (such as hidden memory file 1622) may contain coded or uncoded secret information. In the embodiment of FIG. 16, the party is in possession of a portable storage media, such as a card 1602 having a magnetic stripe for recording information thereon. The card 1602 is issued by an agency, or a bank, during enrollment of the party. Information recorded on the card 1602 includes the party's revisable owner code (ROC), a coded address (CPK) of the hidden file 1622, an agency identification number (AID or Agency ID), and a transaction sequence number (TSN). The party's ROC is generated as described above (see FIG. 6). The coded address CPK of the hidden memory file 1622 may either represent the entire address of the hidden memory file 1622 or only a portion of the address of the hidden memory file 1622, as described above.

The party to be authenticated enters a personal identification number (PIN) at a terminal. The PIN is input to an irreversible coder 1606 to produce a coded personal identification number (CPN). The information recorded on the party's card 1602 is read from the card 1602 using an appropriate reader (not shown). The CPK read from the card 1602 is applied as an input to an uncoder 1612, which also receives the CPN as a key input. The uncoder 1612 uncodes CPK using CPN as a key input to generate PK, which represents either the total address of the hidden memory file 1622 or a portion of the address of the hidden memory file 1622 (as noted above).

The transaction sequence number (TSN) read from the card 1602 is input to a mixer 1608 and then to a coder 1610. The coder 1610 also receives the CPN as a key input. The coder 1610 codes the TSN using the CPN as a key input to generate an anti-duplication VAN (ADVAN). The ADVAN, PK, ROC, and AID are input to a mixer 1614 and the resulting mixed signal is sent to the remote CPU over a preferably unsecured communication link.

The user's hidden memory file 1622 is part of a memory which is used to store such files at the remote CPU. The sorter 1616 separates the received mixed signal into its component parts ROC, PK, AID, and ADVAN. Where the PK generated by the uncoder 1612 is only a portion of the address to the hidden memory file 1622, the AID is used as an index to a memory table 1618 to retrieve other address components for the hidden memory file 1622. Thus, the address components in the memory table 1618 applicable in any given transaction depends on the particular AID. The PK is combined with the other address components at a combiner 1620 to thereby form the composite address of the hidden memory file 1622. The AID could also identify a predetermined procedure for combining the applicable address components. The composite address is used to access the hidden memory file 1622 to retrieve a secret random number RN (which is generated according to the method described above with respect to FIG. 6). RN is input as a key to a uncoder 1624. The uncoder 1624 also receives the ROC from the sorter 1616 and thereby generates CPN.

A transaction sequence number (TSN) is also retrieved from the hidden memory file 1622 and is input to a coder 1632. The coder 1632 also receives CPN as a key input and thereby generates an ADVAN. The ADVAN generated by the coder 1632 is compared with the ADVAN output from the sorter 1616 at a comparator 1630. If a favorable comparison is obtained, then coder 1628 is enabled. If the comparison is not favorable, then the user is not authenticated and does not gain access to the memory file 1622.

Coder 1628 receives PK as an input and CPN as a key and thereby generates CPK. The CPK generated by the coder 1628 is received by an uncoder 1626 as a key input. The uncoder 1626 also receives as input coded information which is retrieved from the hidden memory file 1622. The uncoder 1626 uncodes the coded information from the hidden memory file 1622 using the CPK as a key input to thereby produce clear information. The clear information is then provided to the authenticated user.

As a result of the favorable comparison of the ADVANs at the comparator 1630, a new (or revised) transaction sequence number (TSN) is generated and stored in the hidden memory file 1622. Also, a coder 1634 is enabled. The coder 1634 receives the CPN as an input and also receives a revised RN as a key input. The output of coder 1634 is a new ROC, which is combined with the new TSN in mixer 1635. The mixer 1635 output is sent back to the terminal where the sorter 1604 separates the new TSN and ROC, which are then recorded on the user's card (in order to prepare for the next transaction by the user). Note also that a new CPK may be generated as well by revising a memory address component, such as the address displacement. In this event, the new CPK would also be returned to the terminal to be recorded on the user's card.

It should be noted that an unsecured communication link between the mixer 1614 and the sorter 1616 is utilized if the hidden memory file 1622 is remote from the location where the party's PIN is entered (that is, the terminal). It should also be noted that the transaction sequence number (TSN), in conjunction with the ADVAN, serves to protect the authenticity of the transaction and the user's card against fraudulent duplication of the transaction information (that is, by recording the output of the mixer 1614 and retransmitting it later to the sorter 1616).

A number of additional applications for the present invention will now be described.

The invention could be utilized in a pay telephone system in which calls could be made without the use of money. The call originator uses a telephone in the usual way to enter the telephone number of the party to be called (i.e., to the call recipient). The call originator also enters his own telephone number and PIN. The system then authenticates the identity of the originator as described above (by using, for example, the embodiment depicted in FIGS. 6–8 or in FIGS. 9–12). In the first embodiment (i.e., FIGS. 6, 7, 8A and 8B), the originator's PIN is coded, and used to derive an arbitrary number, which is subsequently compared to another such number which is generated from a reconstituted version of the coded PIN. The reconstituted coded PIN is formed from an RN and ROC which are accessed from the originator's account file, with the originator's telephone number serving as a file index. If the comparison is unfavorable, the call is aborted; otherwise, call processing continues.

In the second embodiment, the originator's telephone number is used as an index to file no. 1 to access an originator's CPKO and true CNO. The originator's coded PIN, CPNO, is then combined with the originator's CPKO to generate a CNO (as in FIG. 12). The originator's identify is then authenticated by comparing the true CNO with the derived CNO. If the comparison is unfavorable, the call is aborted; otherwise, processing continues. The originator can use a machine readable card, or the like which has CPKO and CNO previously recorded thereon. In this event, access to file no. 1 is unnecessary.

In either embodiment, if the identity comparison is favorable, then the originator's credit balance is extracted from the originator's file to determine whether the call should be allowed. If the credit balance is favorable, then the telephone connection is extended to the call recipient, and the recipient's telephone is rung.

At the end of the call, the originator's credit balance is diminished by the cost of the call, and the new balance is computed and rewritten to the originator's file. The originator may then be advised of the cost of the call. When the recipient's telephone rings and the call is answered, the system can require that the identity of the person answering the phone be authenticated, as in a person to person call. In this event, the recipient is asked to enter a PIN, and the recipient's identity is authenticated using either of the two embodiments mentioned above.

Alternatively, a first joint code could be generated when the call is initiated, e.g., from the originator's CPN, and the recipient's reconstituted CPN. When the call is answered, the recipient enters his PIN, which is converted to a CPN and combined with the originator's reconstituted CPN to form a second joint code. A comparison then ensues between the first and second joint codes.

Another application of the invention is a system which uses a bill as the means of (or vehicle for) payment. The bill contains the usual payment information, and a VAN is also recorded on the bill when the bill is generated. The VAN is derived from the payment information (INFO) and identification information associated with the originator of the bill (e.g., similar to the bank identification line of information which appears at the bottom of an originator's check) or the originator's TIN and BIN. The bill may also contain the recipient's TIN and BIN. Preferably, the above information is coded in a standard format, at a fixed location on the bill itself. The bill is then used in an appropriate document reader to provide the transaction payment information to the system. The party paying the bill (i.e., the payor) enters his PIN and the payor is then authenticated using the PIN. Also, the VAN is authenticated (using one of the methods described above). If the payor and the VAN are authentic, the bill is paid. A redemption VAN is generated (using information associated with the payee party) and printed on the bill, when it has been paid.

Alternatively, the payor could simply key in the information from the face of the bill. When the transaction is completed, a redemption VAN is displayed to the payor, which he records on the bill (or the VAN could be automatically recorded on the bill).

In accordance with a further application of the embodiments of this invention, a medical prescription form which has been originated and issued by a doctor to a patient (a recipient), can be authenticated to permit dispensing of the designated medicine, or drug, in a processing jurisdiction, along with automated payment. Automated payment may include a third party such as an insurance provider. This system is particularly useful for a patient who is in desperate need of medicine, and is in a remote or strange environment, where the prescription cannot be easily authenticated, or an available pharmacy cannot be found.

The prescription form contains identification information associated with the doctor and the patient, and the usual information which appears on a prescription, such as the type of medicine, strength, quantity, application, date, refills, generic, and a control number. The prescription form also contains a VAN, which is the result of coding the medical and identification information. Preferably, the information and the VAN are recorded on the prescription form so that it is readable by an individual, and it also includes coded symbols or characters representing the same information in machine readable form.

When the prescription form is utilized by the recipient to obtain the medicine from a processing entity (such as a drug store), the information on the form is read automatically by a terminal of the system, or it is entered via a keyboard. The recipient also enters his PIN, and the system authenticates the prescription form, the doctor, and the recipient in accordance with the embodiments described previously. An indication of the cost of the prescribed medicine, and the method of payment is provided to the recipient. The recipient may elect to pay by using one of the methods described herein.

Note that the processing entity may also include a centralized clearinghouse in communication with dispensing outlets (i.e., drug stores) for authenticating prescriptions. An RVAN may be generated from the VAN and information associated with the processing entity, and then associated with the transaction, to thereby document the processing entity's involvement in the transaction.

If a patient attempts to use a prescription in a state where the originating physician is not licensed, such as out of state, the original prescription may not be usable. In this situation, a directory system of predetermined licensed "correspondent" physicians may be established, and a correspondent physician can automatically authorize the prescription of an originating physician (on-line), after the original prescription is authenticated.

The invention also finds utility in a paperless/cashless transaction system, in which "funds transfer" transactions, such as purchases, occur without the use of money, or checks. In this system, the payment originator uses a payment recipient's terminal which stores information to identify the precise location of the recipient's account. Alternatively, an originator PIN, information identifying an originator account and a recipient account, and funds transfer information (INFO) which includes a payment amount are entered directly into a terminal of this system by the payment originator. The system initially generates a VAN, (OVAN), by using the payment information (INFO) in conjunction with the identification information associated with the payment originator and payment recipient. The payment originator is authenticated using the originator PIN using a method described above. The system then approves or disapproves the payment based upon an authentication of the VAN, and the "joint" identification information associated with the participants, and the availability of funds, or credit. Such transactions are carried on entirely electronically, the participant's bank accounts are credited and debited automatically, allowing commercial transactions to be completed "instantaneously". An RVAN may be generated using the INFO and printed on a receipt which is dispensed to the originator.

Although preferred embodiments of the invention have been disclosed for illustrative purposes, those skilled in the art will appreciate that many additions, modifications, and substitutions are possible without departing from the scope or spirit of the invention as defined in the accompanying claims.

I claim:

1. In a system wherein a party has a personal identification number from which first coded authentication information is generated, the first coded authentication information being derivable from a predetermined secret number and a predetermined non-secret number which have been previously stored in a storage means, a method for authenticating the party comprising the steps of:

receiving the personal identification number from the party, the personal identification number being unrecoverable in the system;

generating second coded authentication information by using the received personal identification number, the step of generating the second coded authentication information comprises the steps of coding the received personal identification number to generate a coded personal identification number and coding an arbitrary number using the coded personal identification number to generate a first coded arbitrary number;

retrieving the secret and non-secret numbers from the storage means;

generating third coded authentication information by using the retrieved secret and non-secret numbers;

comparing the second coded authentication information and the third coded authentication information;

authenticating the party if the second coded authentication information corresponds to the third coded authentication information; and generating at a first site an anti-duplication variable authentication number (ADVAN) by coding at least a transmission date and time with the first coded authentication information, and further including the step of transmitting the ADVAN, the first coded arbitrary number and the arbitrary number from a first site to a second site over an unsecured communication medium.

2. The method of claim 1, further comprising the steps of:
deriving at the second site the first coded authentication information from the retrieved secret and non-secret numbers;

uncoding the ADVAN at the second site using the derived first coded authentication information to regenerate the transmission date and time; and further authenticating the party if the regenerated transmission date and time correspond to a reception date and time.

3. In a transaction system wherein a party has a first personal identification number (PIN1) and an official has a second personal identification number (PIN2), a method for enrolling the party and issuing the party a credential, and then authenticating the party and the credential in a subsequent transaction, the method of enrolling and issuing comprising the steps of:

coding information associated with the party with information associated with the official to generate a joint code;

storing the joint code in a first storage means, the joint code being retrievable from the first storage means only by a party who can provide the PIN1;

storing the joint code in a second storage means, the joint code being retrievable from the second storage means only by a party who can provide the PIN2;

coding information relevant to the credential with the joint code to generate a first variable authentication number (VAN1);

recording the VAN1 on the credential;

issuing the credential to the party; and the method of authenticating the party and the credential in a subsequent transaction comprising the steps of:

receiving the PIN1 from the party to be authenticated;

accessing the first storage means with the PIN1 to locate and retrieve the joint code;

coding information relevant to the credential with the retrieved joint code to generate a second variable authentication number (VAN2);

comparing the VAN2 to the VAN1; and authenticating the party and the credential if the VAN2 corresponds to the VAN1.

4. The method of claim 3, further comprising the steps of:

retrieving the joint code from the second storage means;

regenerating the joint code by coding information associated with the party with information associated with the official;

comparing the retrieved joint code with the regenerated joint code; and authenticating the official if the retrieved joint code corresponds to the regenerated joint code.

5. The method of claim 3, further comprising the steps of:

retrieving the joint code from the first storage means;

retrieving the joint code from the second storage means;

comparing the retrieved joint codes; and authenticating the official if the retrieved joint codes correspond.

6. The method of claim 3 wherein the joint code is revised or erased from the second storage means after the VAN1 is recorded on the credential.

7. A transaction system for enrolling a party, wherein the party has a first personal identification number (PIN) and the system has an official, the system comprising:

means for coding information associated with the party with information associated with the official to generate a joint code, the joint code being subsequently associable with a transaction;

a storage means being accessible only to a party with knowledge of the first PIN;

means for storing the joint code in the storage means, such that if no party exists with knowledge of the first PIN, the joint code cannot be accessed from the storage means and, therefore, cannot be associated with a transaction;

means for coding information relevant to the transaction with the joint code for generating a variable authentication number (VAN);

means for recording the VAN on a credential associated with the transaction; and means for issuing the credential.

8. A transaction system for enrolling a party, wherein the party has a first personal identification number (PIN) and the system has an official, the system comprising:

means for coding information associated with the party with information associated with the official to generate a joint code, the joint code being subsequently associable with a transaction;

a storage means being accessible only to a party with knowledge of the first PIN; and means for storing the joint code in the storage means, such that if no party exists with knowledge of the first PIN, the joint code cannot be accessed from the storage means and, therefore, cannot be associated with a transaction;

means for storing the joint code in a second storage means accessible only to a party having knowledge of the second PIN;

means for receiving the second PIN from the official;

means for accessing the second storage means using at least the received second PIN for retrieving the joint code;

means for coding information relevant to the transaction using the joint code for generating a variable authentication number (VAN);

means for recording the VAN on a credential associated with the transaction; and means for issuing the credential such that a party without knowledge of the second PIN cannot access the second storage means or the joint code stored therein and, therefore, cannot legitimately issue the credential.

9. A transaction system according to claim 7 further including:

means for storing in the storage means the information associated with the party and the information associated with the official that are used to generate the joint code.

10. In a system wherein a party has a personal identification number from which first coded authentication information is generated, the first coded authentication information being derivable from a predetermined secret number and a predetermined non-secret number which have been previously stored in a storage means, a method for authenticating the party and a transaction comprising the steps of:

receiving at a first site a personal identification number from the party, the personal identification number being unrecoverable in the system;

generating second coded authentication information using the received personal identification number;

generating a first anti-duplication variable authentication number (ADVAN1) by coding at least a transmission date and time, and other transaction information using the second coded authentication information, the transmission date and time being unique and non-predetermined;

transmitting at least the first anti-duplication variable authentication number (ADVAN1) and the transmission date and time from the first site to a second site;

receiving at the second site at least the first anti-duplication variable authentication number (ADVAN1) and the transmission date and time;

retrieving at the second site the secret and non-secret numbers from the storage means;

generating third coded authentication information using the retrieved secret and non-secret numbers;

uncoding the first anti-duplication variable number (ADVAN1) using the third coded authentication information to recover at least the transmission date and time and the other transaction information, comparing at least the transmission date and time recovered from the first anti-duplication variable authentication number (ADVAN1) with at least the transmission date and time received at the second site; and authenticating the party and the transaction if at least the transmission date and time recovered from the first anti-duplication variable authentication number (ADVAN1) corresponds to the transmission date and time received at the second site.

11. The method of claim 10 comprising the additional steps of:

coding the first transmission date and time received at the second site and the other transaction information recovered by uncoding the first anti-duplication variable authentication number (ADVAN1) using the third coded authentication information to generate a second anti-duplication variable authentication number (ADVAN2);

comparing the first anti-duplication variable authentication number (ADVAN1) with the second anti-duplication variable authentication number (ADVAN2); and authenticating the party and the transaction if the first anti-duplication variable authentication number (ADVAN1) corresponds to the second anti-duplication variable authentication number (ADVAN2).

12. In a system wherein a party has a personal identification number from which first coded authentication information is generated, the first coded authentication information being derivable from a predetermined secret number and a predetermined non-secret number which have been previously stored in a storage means, a method for authenticating the party and a transaction comprising the steps of:

receiving at a first site a personal identification number from the party, the personal identification number being unrecoverable in the system;

generating second coded authentication information using the received personal identification number;

generating an anti-duplication variable authentication number (ADVAN) by coding at least a first transmission date and time, and other transaction information using the second coded authentication information, the first transmission date and time being unique and non-predetermined;

transmitting at least the anti-duplication variable authentication number (ADVAN) from the first site to a second site;

receiving at the second site at least the anti-duplication variable authentication number (ADVAN);

retrieving at the second site the secret and non-secret numbers from the storage means;

generating third coded authentication information using the retrieved secret and non-secret numbers;

uncoding the anti-duplication variable authentication number (ADVAN) received at the second site using the third coded authentication information to recover at least the first transmission date and time;

comparing at least the first transmission date and time recovered from the anti-duplication variable authentication number (ADVAN) with at least a second date and time of receiving the anti-duplication variable authentication number (ADVAN); and authenticating the party and the transaction if at least the first transmission date and time recovered from the anti-duplication variable authentication number (ADVAN) compares favorably to the second date and time of receiving the anti-duplication variable authentication number (ADVAN).

13. A method for authenticating a credential and a first party who was issued the credential, and a second party associated with issuing the credential, the method comprising the steps of:

retrieving first information previously stored in the credential, wherein the first information previously stored in the credential includes a first variable authentication number (VAN1);

retrieving second information previously stored in a storage means associated with at least one of the parties, wherein the second information includes a joint code;

receiving third information from at least one of the parties;

coding the third information from at least one of the parties, and the joint code retrieved from the storage means to generate a second variable authentication number (VAN2); and authenticating the credential, and the first party who was issued the credential, and the second party associated with issuing the credential, if the first variable authentication number (VAN1) retrieved from the credential corresponds to the generated second variable authentication number (VAN2).

14. The method of claim 13, wherein the third information received from at least one of the parties comprises identification information associated with at least one of the parties.

15. The method of claim 13 wherein the second party is an agent, or an agency, or an official of an agency, or an authority, or an administrator, or an entity entrusted with issuing a credential.

16. A method for enrolling and issuing a credential to a first party by a second party, the information stored in the credential comprising first non-secret information associated with the first party, and second non-secret information associated with the second party, and other information associated with the credential, and a variable authentication number (VAN) derived from at least third information associated with one of the parties, and fourth information associated with the other party, the method comprising the steps of;

receiving first non-secret information associated with the first party, and second non-secret information associated with the second party, and the other information associated with the credential;

receiving third information associated with one of the parties, and fourth information associated with the other party;

coding the third information associated with one of the parties, and the fourth information associated with the other party to generate a variable authentication number (VAN);

storing the first non-secret information associated with the first party, and the second non-secret information associated with the second party, and the other information associated with the credential, and the variable authentication number (VAN) in the credential; and issuing the credential to the first party.

17. The method of claim 16 comprising the additional step of;

storing at least a portion of the information stored in the credential, and at least a portion of the information used to derive the VAN in at least one storage means associated with at least one of the parties.

18. The method of claim 16 wherein the fourth information associated with one of the parties is stored in the storage means associated with at least one of the parties and comprises a secret number.

19. The method of claim 16 wherein the third information associated with one of the parties comprises a coded number derived in conjunction with the PIN of that party.

20. The method of claim 16 wherein the fourth information associated with one of the parties comprises a coded number derived in conjunction with the PIN of that party.

21. The method of claim 16 wherein a first joint key is generated and stored in at least one storage means associated with the at least one of the parties, the method comprising the steps of;

coding the third information associated with one of the parties, and the fourth information associated with the other party to generate the first joint key; and storing the first joint key in at least one storage means associated with the at least one of the parties.

22. The method of claim 16 wherein the second party is an agent, or an agency, or an official of an agency, or an authority, or an administrator, or an entity entrusted with issuing a credential.

23. A method for securing in escrow, and in trust, information associated with a first party in a storage means associated with a second party, wherein at least a portion of the escrowed information is used for generating a joint key, wherein the joint key is derivable from information associated with the first party and information associated with a second party, the first party being enrolled by the second party and issued a credential, wherein the escrowed information comprises at least a variable authentication number (VAN), the VAN being previously derived from the information used to generate the joint key and other information, the method comprising the steps of:

previously receiving information associated with the first party and information associated with the second party;

previously generating a joint key using information associated with the first party and information associated with the second party; and retaining in the storage means, in trust, at least the information associated with the first party and information associated with the second party which was previously used to generate the joint key.

* * * * *